United States Patent
Tsubuku

(10) Patent No.: US 9,750,523 B2
(45) Date of Patent: *Sep. 5, 2017

(54) ULTRASONIC TREATMENT APPARATUS

(71) Applicant: OLYMPUS CORPORATION, Hachioji-shi, Tokyo (JP)

(72) Inventor: Yoshihiro Tsubuku, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,858

(22) Filed: Jul. 27, 2016

(65) Prior Publication Data

US 2016/0331399 A1    Nov. 17, 2016

Related U.S. Application Data

(63) Continuation of application No. PCT/JP2015/052865, filed on Feb. 2, 2015.

(30) Foreign Application Priority Data

Feb. 17, 2014   (JP) ................................. 2014-027988

(51) Int. Cl.
*B06B 1/06* (2006.01)
*H01L 41/04* (2006.01)
(Continued)

(52) U.S. Cl.
CPC ........ *A61B 17/320092* (2013.01); *B06B 1/06* (2013.01); *H01L 41/042* (2013.01);
(Continued)

(58) Field of Classification Search
CPC ........ B06B 1/06; B06B 1/0603; B06B 1/0607
(Continued)

(56) References Cited

U.S. PATENT DOCUMENTS 4,979,952 A   12/1990 Kubota et al.
8,303,579 B2  11/2012 Shibata
(Continued)

FOREIGN PATENT DOCUMENTS

| JP | S63-212342 A   | 9/1988  |
|----|----------------|---------|
| JP | 2009-254818 A  | 11/2009 |
| WO | 2010/076869 A1 | 7/2010  |

OTHER PUBLICATIONS

Sep. 1, 2016 International Preliminary Report on Patentability issued in International Application No. PCT/JP2015/052865.
(Continued)

*Primary Examiner* — Derek Rosenau
(74) *Attorney, Agent, or Firm* — Oliff PLC

(57) ABSTRACT

A ultrasonic treatment apparatus includes a gradual decrease detecting section detecting a gradual decrease start point at which a ultrasonic impedance value starts to gradually decrease, and a peak judging section judging whether or not a held tentative peak value that is a ultrasonic impedance value at the gradual decrease start point is a target peak. The ultrasonic treatment apparatus includes an ultrasonic control section outputting a vibration generating electric power in a second ultrasonic output mode where incision performance provided by an ultrasonic vibration becomes smaller than that in a first ultrasonic output mode before a peak detection point, when at least a prescribed time passes from the peak detection point at which the target peak is detected.

12 Claims, 10 Drawing Sheets

(51) Int. Cl.
*A61B 17/32* (2006.01)
*A61B 18/14* (2006.01)
*A61B 18/00* (2006.01)
*A61B 17/00* (2006.01)

(52) U.S. Cl.
CPC . *A61B 18/1445* (2013.01); *A61B 2017/00026* (2013.01); *A61B 2017/00115* (2013.01); *A61B 2017/00132* (2013.01); *A61B 2017/00137* (2013.01); *A61B 2018/00994* (2013.01)

(58) Field of Classification Search
USPC ........ 310/322, 334, 335, 317; 600/437, 439, 600/459
See application file for complete search history.

(56) References Cited

U.S. PATENT DOCUMENTS

| | | |
|---|---|---|
| 2009/0259221 A1 | 10/2009 | Tahara et al. |
| 2010/0168742 A1 | 7/2010 | Shibata |
| 2010/0179423 A1* | 7/2010 | Ramstein ........... A61B 5/02007 600/437 |
| 2011/0290853 A1* | 12/2011 | Shelton, IV ..... A61B 17/07207 227/177.1 |
| 2012/0310264 A1 | 12/2012 | Messerly et al. |

OTHER PUBLICATIONS

Mar. 24, 2015 Search Report issued in International Patent Application No. PCT/JP2015/052865.

\* cited by examiner

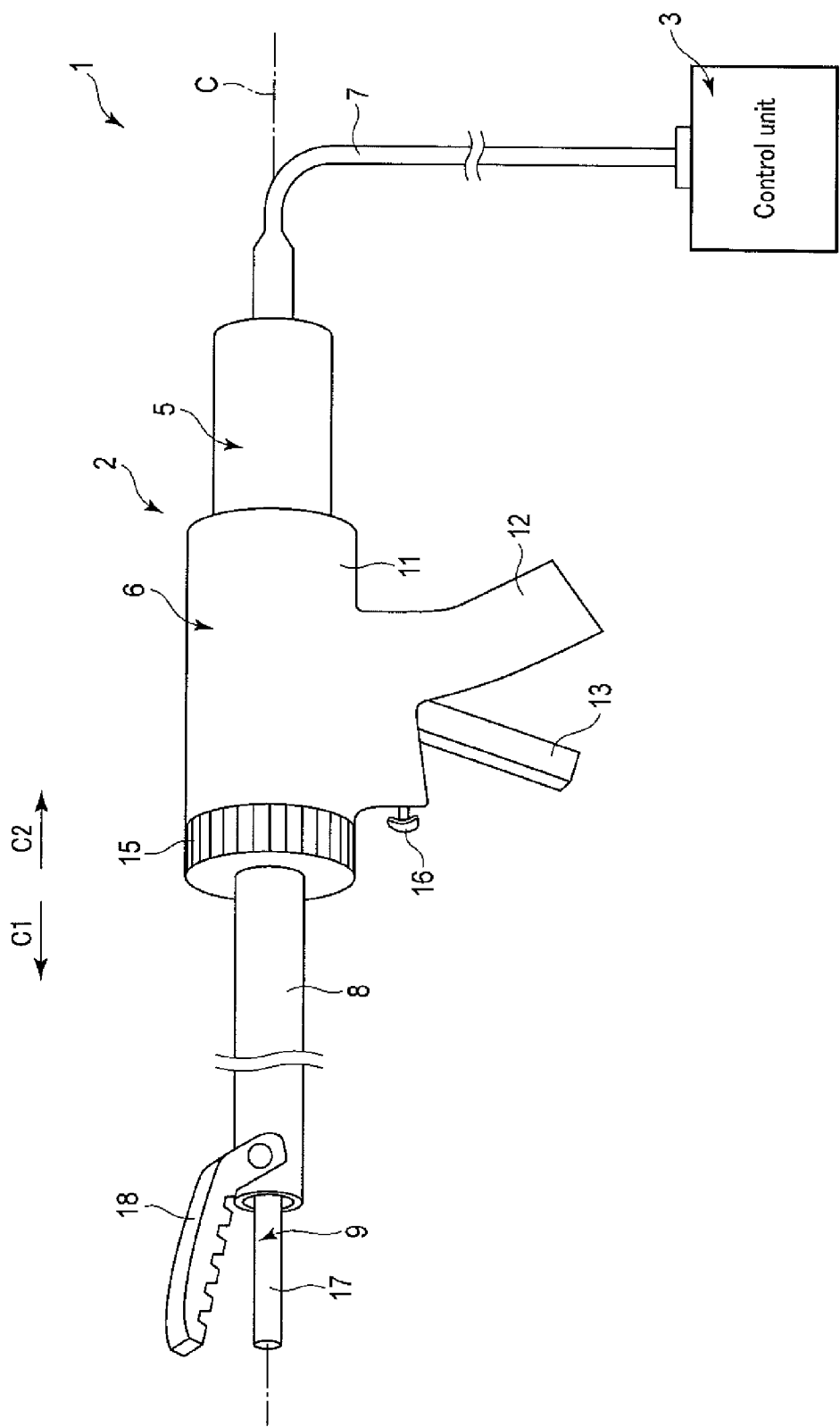
F I G. 1

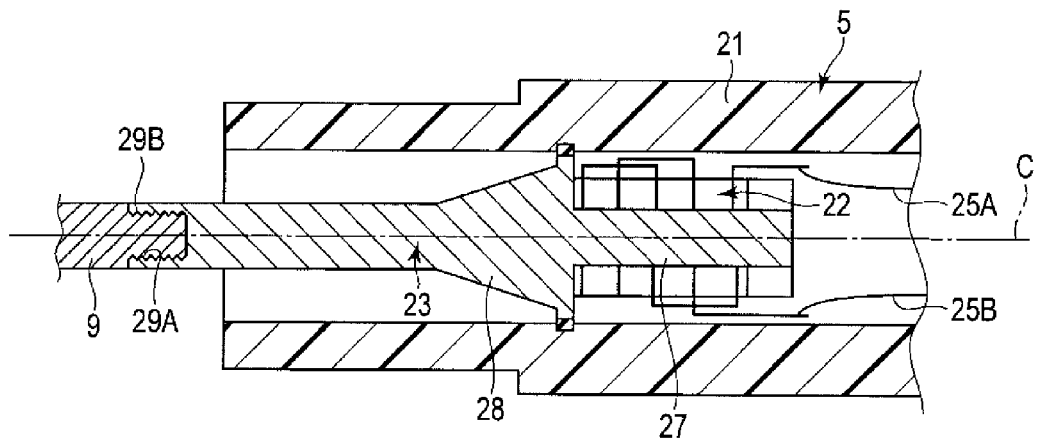
F I G. 2
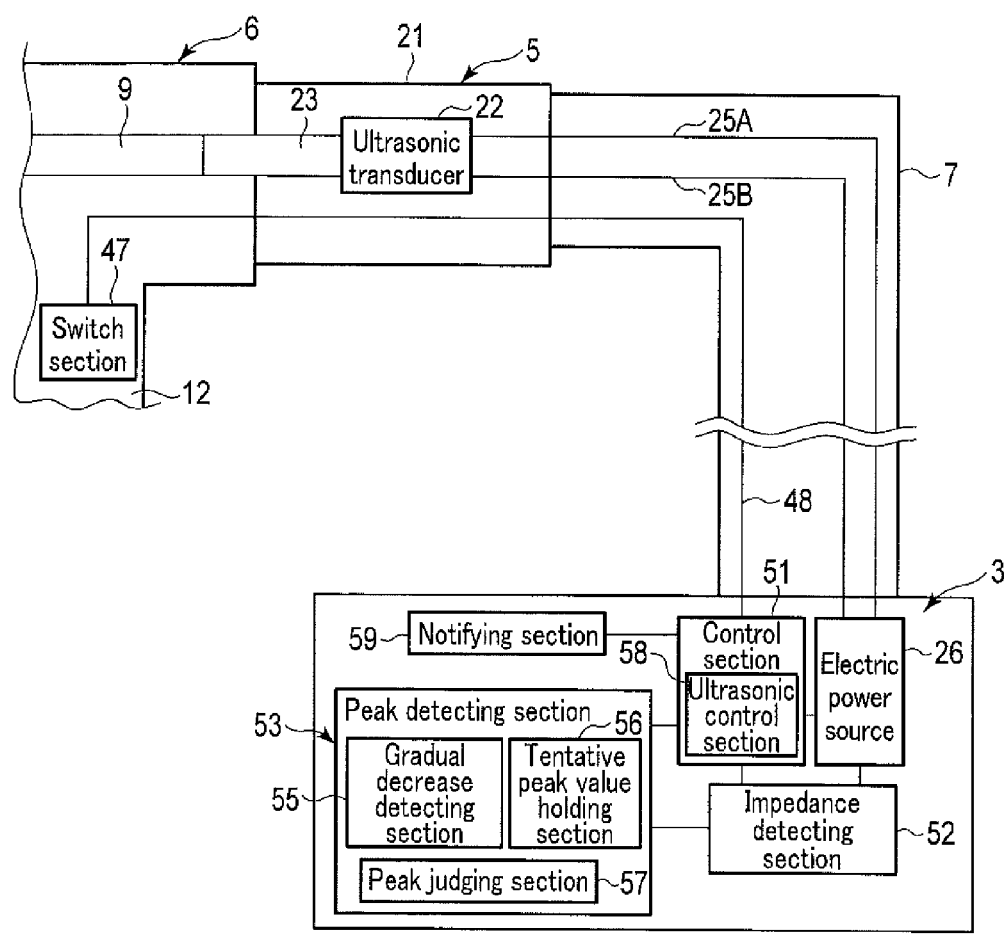
F I G. 3

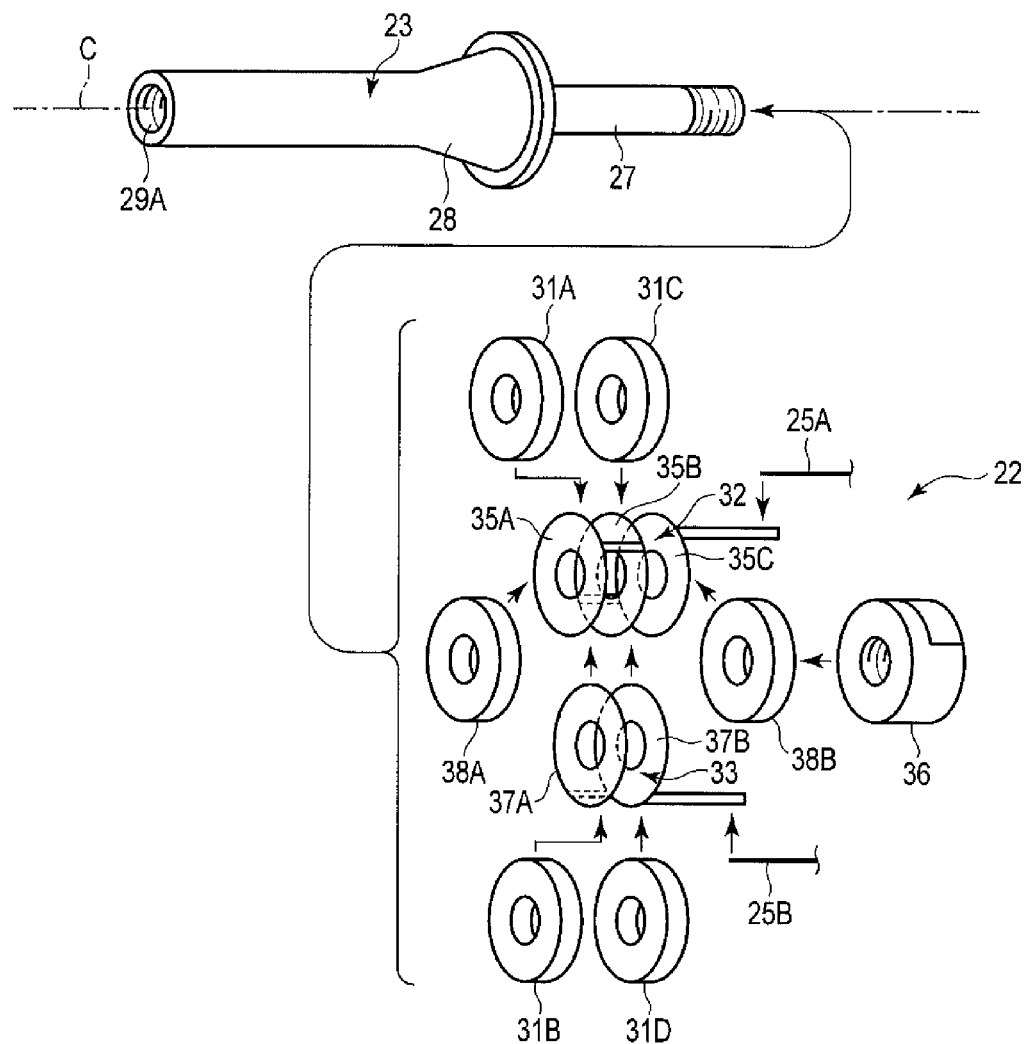
F I G. 4
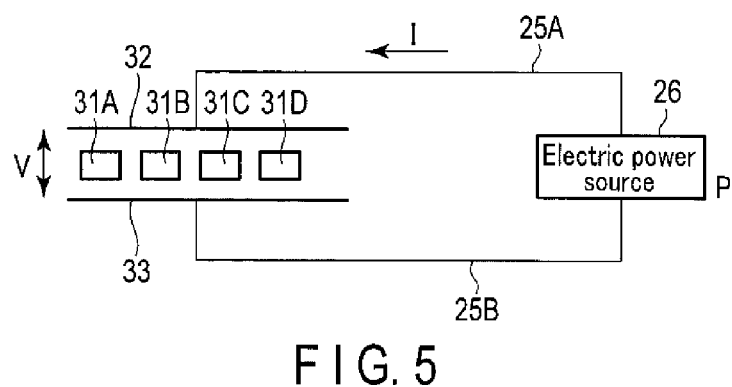
F I G. 5

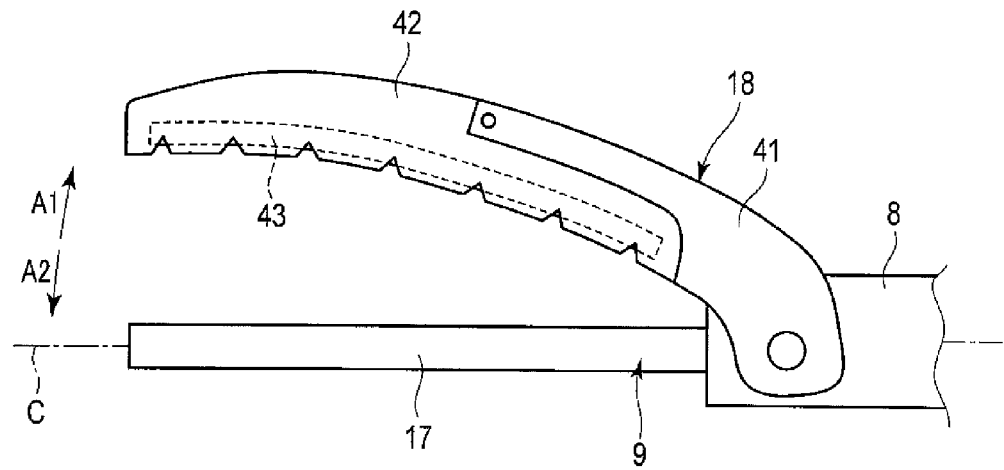
F I G. 6
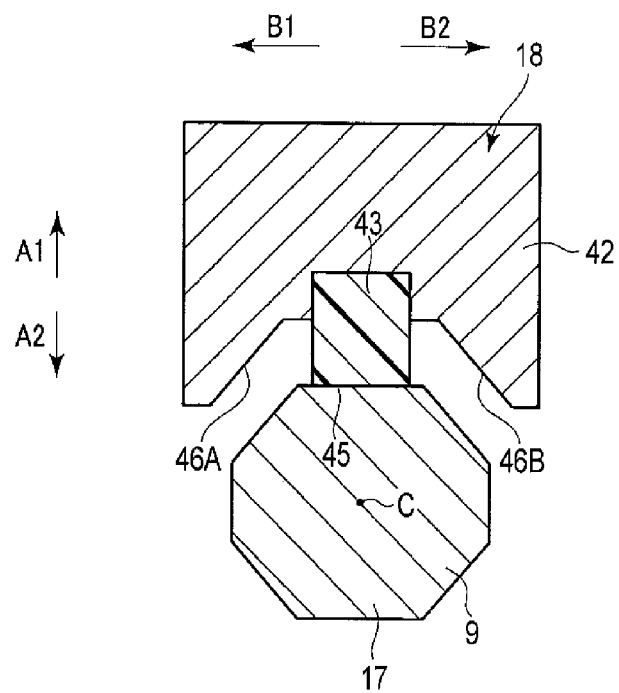
F I G. 7

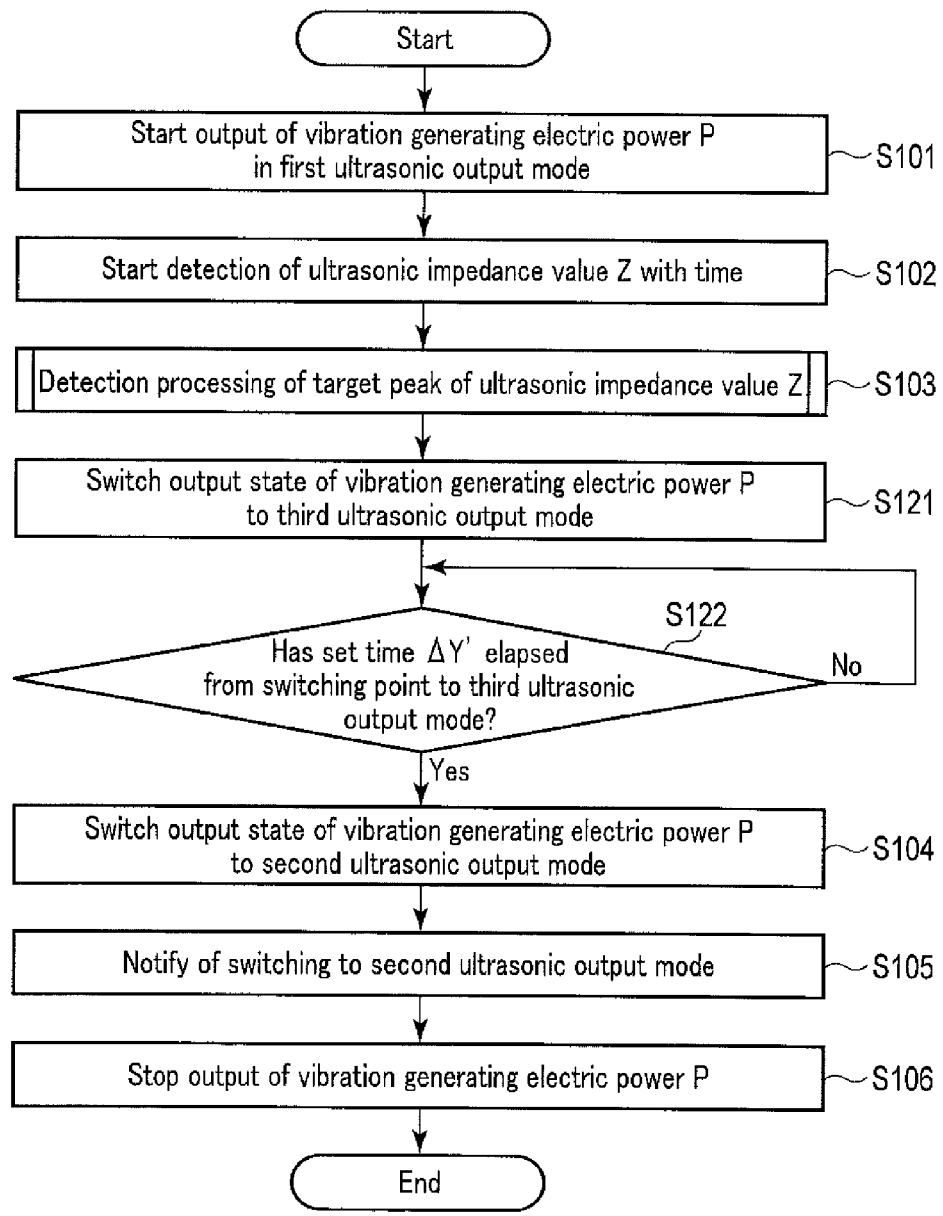
F I G. 16

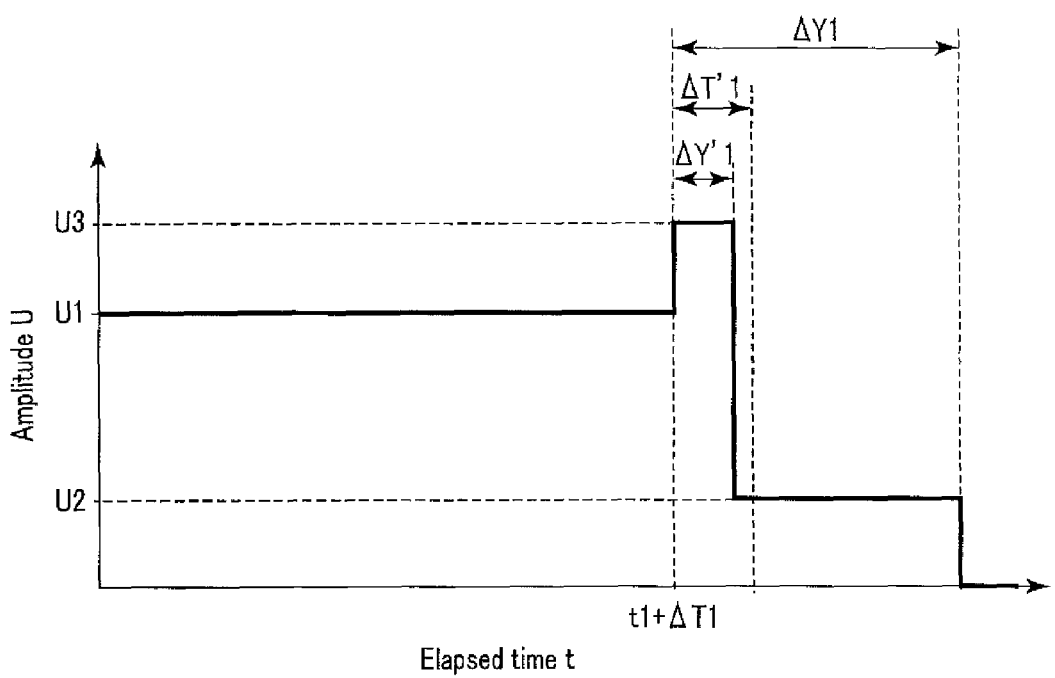
F I G. 17

ULTRASONIC TREATMENT APPARATUS

CROSS-REFERENCE TO RELATED APPLICATIONS

This is a Continuation Application of PCT Application No. PCT/JP2015/052865, filed Feb. 2, 2015 and based upon and claiming the benefit of priority from prior Japanese Patent Application No. 2014-027988, filed Feb. 17, 2014, the entire contents of which are incorporated herein by reference.

BACKGROUND OF THE INVENTION

1. Field of the Invention

The present invention relates to an ultrasonic treatment apparatus which grasps a treated target between a treatment section to which an ultrasonic vibration is transmitted and a jaw openable and closable relative to the treatment section, so as to treat the grasped treated target by use of the ultrasonic vibration.

2. Description of the Related Art

For example, U.S. Patent Application Publication No. 2012/0310264 discloses an ultrasonic treatment apparatus which includes a treatment section to which an ultrasonic vibration is transmitted and a jaw openable and closable relative to the treatment section. In this ultrasonic treatment apparatus, when vibration generating electric power is transmitted from an electric power source to a vibration generating section, the ultrasonic vibration is generated in an ultrasonic transducer which is the vibration generating section. Then, the generated ultrasonic vibration is transmitted to the treatment section, and the treatment section treats a treated target such as a biological tissue by use of the transmitted ultrasonic vibration. Here, opening and closing directions of the jaw are perpendicular (transverse) to a transmitting direction of the ultrasonic vibration. When the ultrasonic vibration is transmitted to the treatment section in a state where the treated target is grasped between the treatment section and the jaw, frictional heat is generated between the treated target and the treatment section. By the frictional heat, the treated target is coagulated and simultaneously incised. Furthermore, in the ultrasonic treatment apparatus, an ultrasonic impedance value of the vibration generating electric power is detected with time, and it is judged whether the ultrasonic impedance value is within a range of a first default threshold or more and a second default threshold or less, the second threshold being greater than the first threshold.

BRIEF SUMMARY OF THE INVENTION

According to one aspect of the invention, an ultrasonic treatment apparatus includes that: an electric power source configured to output a vibration generating electric power; a vibration generating section configured to generate an ultrasonic vibration when the vibration generating electric power is supplied from the electric power source; a treatment section to which the ultrasonic vibration generated in the vibration generating section is transmitted, and which is configured to perform a treatment by use of the transmitted ultrasonic vibration; a jaw which is openable and closable relative to the treatment section, and which includes a contact section contactable with the treatment section in a state where the jaw is closed relative to the treatment section; an impedance detecting section configured to detect an ultrasonic impedance value of the vibration generating electric power with time, in a state where the vibration generating electric power is output from the electric power source; a gradual decrease detecting section configured to detect a gradual decrease start point at which the ultrasonic impedance value starts to gradually decrease on the basis of detection results in the impedance detecting section; a tentative peak value holding section configured to hold the ultrasonic impedance value at the detected gradual decrease start point as a tentative peak value; a peak judging section configured to judge whether or not the held tentative peak value is a target peak of a detection target by comparing, to the held tentative peak value, changes with time of the ultrasonic impedance value after the gradual decrease start point; and an ultrasonic control section configured to control an output state of the vibration generating electric power from the electric power source, the ultrasonic control section being configured to output the vibration generating electric power from the electric power source in a second ultrasonic output mode where incision performance provided by the ultrasonic vibration in the treatment section becomes smaller than that in a first ultrasonic output mode before a peak detection point on the basis of a determination in the peak judging section, when at least a prescribed time passes from the peak detection point at which the target peak is detected.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an ultrasonic treatment apparatus according to a first embodiment;

FIG. 2 is a longitudinal cross-sectional view schematically showing a configuration of a transducer unit according to the first embodiment;

FIG. 3 is a schematic view showing an electrical connection state of the transducer unit and a control unit according to the first embodiment;

FIG. 4 is a schematic exploded perspective view showing each member in a horn member and an ultrasonic transducer according to the first embodiment;

FIG. 5 is a schematic view showing an electrical connection state between the ultrasonic transducer and an electric power source according to the first embodiment;

FIG. 6 is a side elevation schematically showing a treatment section and a jaw according to the first embodiment;

FIG. 7 is a transverse cross-sectional view schematically showing cross sections of the treatment section and the jaw perpendicular to a longitudinal axis according to the first embodiment;

FIG. 16 is a flowchart showing an actuating state of the control unit from a start of output of a vibration generating electric power according to a fourth modification; and FIG. 17 is a schematic view showing an example of changes with time of an amplitude of the ultrasonic vibration in the treatment section according to the fourth modification.

DETAILED DESCRIPTION OF THE INVENTION

First Embodiment

Figure 8:
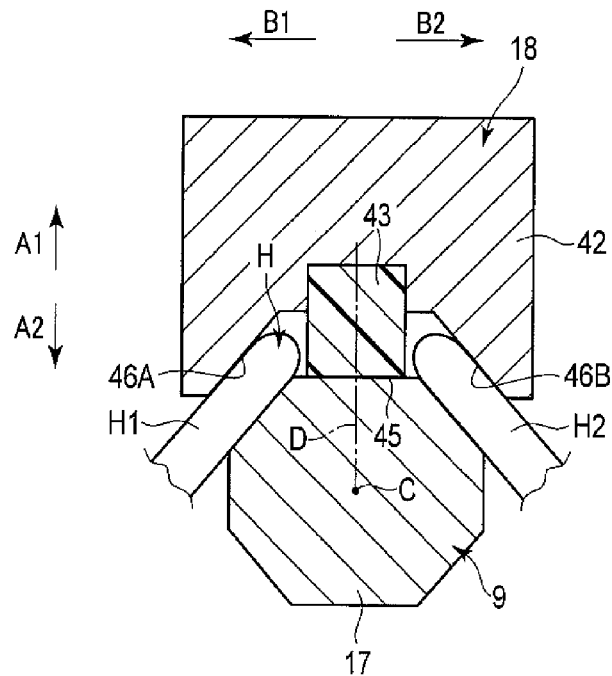
FIG. 8 is a schematic view for explaining cut and divided of a treated target grasped between the treatment section and the jaw according to the first embodiment.

A first embodiment according to the present invention will now be described with reference to FIG. 1 to FIG. 12. FIG. 1 is a view showing an ultrasonic treatment apparatus 1. As shown in FIG. 1, the ultrasonic treatment system 1 includes an ultrasonic treatment instrument (a hand piece) 2, and a control unit (an energy control device) 3. The ultrasonic treatment tool 2 has a longitudinal axis C. One of two directions parallel to the longitudinal axis C is a distal direction (a direction of an arrow C1 in FIG. 1), and an opposite direction of the distal direction is a proximal direction (a direction of an arrow C2 in FIG. 1). The ultrasonic treatment instrument 2 includes a transducer unit 5, and a handle unit 6. The vibrator unit 5 is detachably coupled with a proximal direction side of the handle unit 6. One end of a cable 7 is connected to a proximal portion of the transducer unit 5. The other end of the cable 7 is connected to the control unit 3.

The handle unit 6 includes a tubular case portion 11 extended along the longitudinal axis C, a fixed handle 12 integrally formed with the tubular case portion 11, and a movable handle 13 coupled to the tubular case portion 11 to allow its turning motion. The fixed handle 12 is extended in a state that it is apart from the tubular case portion 11 to the longitudinal axis C. When the movable handle 13 turns around a position at which it is attached to the tubular case portion 11, the movable handle 13 opens or closes relative to the fixed handle 12. Further, the handle unit 6 includes a rotary operation knob 15 attached on a distal direction side of the tubular case portion 11. The rotary operation knob 15 can rotate around the longitudinal axis C relative to the tubular case portion 11. Furthermore, an energy operation input button 16 which is an energy operation input section is provided to the fixed handle 12.

The ultrasonic treatment instrument 2 includes a sheath 8 extended along the longitudinal axis C. The sheath 8 is inserted into the rotary operation knob 15 and into the tubular case portion 11 from the distal direction side, and the sheath 8 is attached to the handle unit 6. Moreover, the ultrasonic treatment instrument 2 includes an ultrasonic probe 9. The ultrasonic probe 9 is extended along the longitudinal axis C from an inside of the tubular case portion 11 through an inside of the sheath 8. The ultrasonic probe 9 is inserted through the sheath 8. Additionally, a treatment section 17 protruding from a distal end of the sheath 8 toward the distal direction is provided in a distal portion of the ultrasonic probe 9.

A jaw 18 is attached to the distal portion of the sheath 8 to allow its turning motion. Inside the tubular case portion 11, the movable handle 13 is connected to a movable tubular portion (not shown) that is arranged in a region located on an inner peripheral direction side of the sheath 8. A distal end of the movable tubular portion is connected to the jaw 18. When the movable handle 13 is opened or closed relative to the fixed handle 12, the movable tubular portion moves along the longitudinal axis C. Consequently, the jaw 18 turns around a position at which it is attached to the sheath 8. When the jaw 18 pivots relative the sheath 8, the jaw 18 is opened or closed relative to the treatment section 17. The sheath 8, the ultrasonic probe 9, and the jaw 18 can rotate together with the rotary operation knob 15 around the longitudinal axis C relative to the tubular case portion 11.

Further, the transducer unit 5 includes a transducer case 21. When the vibrator case 21 is inserted into the tubular case portion 11 from the proximal direction side, the transducer unit 5 is coupled to the handle unit 6. Inside the tubular case portion 11, the vibrator case 21 is coupled with the sheath 8. The oscillator case 21 can rotate together with the rotary operation knob 15 around the longitudinal axis C relative to the tubular case portion 11.

FIG. 2 is a view showing a configuration of the transducer unit 5. As shown in FIG. 2, the transducer unit 5 includes the transducer case 21, an ultrasonic transducer 22 which is a vibration generating section provided inside the vibrator case 21, and a horn member 23 to which the ultrasonic vibrator 22 is attached. FIG. 3 is a view showing an electrical connection state of the transducer unit 5, and the control unit 3. As shown in FIG. 2 and FIG. 3, one end of each of electrical wiring portions 25A and 25B is connected to the ultrasonic oscillator 22. The control unit 3 includes an electric power source 26 that can output a vibration generating electric power P. In the electric power source 26, for example, an electric power from, e.g., a receptacle outlet is converted into the vibration generating electric power P by a conversion circuit or the like, and the vibration generating electric power P is output. The other end of each of the electrical wiring portions 25A and 25B is connected to the electric power source 26. The vibration generating electric power P output from the electric power source 26 is supplied to the ultrasonic transducer 22 through the electrical wiring portions 25A and 25B. When the vibration generating electric power P is supplied, an ultrasonic vibration is produced in the ultrasonic transducer 22.

A transducer mounting portion 27 to which the ultrasonic transducer 22 is mounted is provided to the horn member 23. The ultrasonic vibration produced by the ultrasonic vibrator 22 is transmitted to the horn member 23. Furthermore, a sectional area change portion 28 is provided to the horn member 23 on the distal direction side with respect to the transducer mounting portion 27. In the sectional area change portion 28, a sectional area perpendicular to the longitudinal axis C decreases toward the distal direction. The sectional area change portion 28 enlarges an amplitude of the ultrasonic vibration. A female screw portion 29A is provided in a distal portion of the horn member 23. Moreover, a male screw portion 29B is provided in a proximal portion of the ultrasonic probe 9. When the male screw portion 29B is screwed into the female screw portion 29A, the ultrasonic probe 9 is connected to the distal direction side of the horn member 23. The ultrasonic probe 9 is connected to the horn member 23 inside the tubular case portion 11.

The ultrasonic vibration transmitted to the horn member 23 is transmitted from the proximal direction toward the distal direction along the longitudinal axis C in the horn member 23 and the ultrasonic probe 9. That is, the horn member 23 and the ultrasonic probe 9 are a vibration transmitting section configured to transmit the generated ultrasonic vibration. The ultrasonic vibration is transmitted toward the distal direction until it reaches the treatment section 17. The treatment section 17 gives a treatment to a treated target such as a biotissue by using the transmitted ultrasonic vibration. It is to be noted that, in the vibration transmitting section (the horn member 23 and the ultrasonic probe 9), the proximal end (the proximal end of the horn member 23) and the distal end (the distal end of the ultrasonic probe 9) are antinode positions of the ultrasonic vibrations. Additionally, the ultrasonic vibration is a longitudinal vibration whose vibrating direction and whose transmitting direction are parallel to the longitudinal axis C (the longitudinal direction). Thus, the distal direction parallel to the longitudinal axis C is the transmitting direction of the ultrasonic vibration. Further, in a state where the vibration transmitting section is transmitting the ultrasonic vibration, the vibration transmitting section including the treatment section 17 vibrates at a given resonance frequency F.

FIG. 4 is an exploded view showing each member in the horn member 23 and the ultrasonic transducer 22. As shown in FIG. 4, the ultrasonic vibrator 22 includes (four in this embodiment) ring-like piezoelectric elements 31A to 31D. The vibrator mounting portion 27 of the horn member 23 is inserted through the respective piezoelectric elements 31A to 31D. Further, the respective piezoelectric elements 31A to 31D are disposed on the transducer mounting portion 27 in a state that each of their thickness direction is parallel to the transmitting direction of the ultrasonic vibration (i.e., the longitudinal axis C) and each of their radial direction is perpendicular to the transmitting direction of the ultrasonic vibration (i.e., the distal end direction).

The ultrasonic oscillator 22 includes a first electrode portion 32 and a second electrode portion 33. One end of the electrical wiring portion 25A is connected to the first electrode portion 32, and one end of the electrical wiring portion 25B is connected to the second electrode portion 33. The first electrode portion 32 includes first electrode ring portions 35A to 35C. The first electrode ring portion 35A is placed on the distal direction side of the piezoelectric element 31A, and the first electrode ring portion 35B is placed between the piezoelectric element 31B and the piezoelectric element 31C in the longitudinal axial direction parallel to the longitudinal axis C. Furthermore, the first electrode ring unit 35C is placed on the proximal direction side of the piezoelectric element 31D. The transducer mounting portion 27 is inserted through the respective first electrode ring portions 35A to 35C.

The second electrode portion 33 includes second electrode ring portions 37A and 37B. The second electrode ring portion 37A is placed between the piezoelectric element 31A and the piezoelectric element 31B in the longitudinal axial direction parallel to the longitudinal axis C. Moreover, the second electrode ring portion 37B is placed between the piezoelectric element 31C and the piezoelectric element 31D in the longitudinal axial direction. The vibrator mounting unit 27 is inserted through the respective second electrode ring portions 37A and 37B.

With the above-described configuration, the piezoelectric element 31A is held between the first electrode ring portion 35A and the second electrode ring portion 37A, and the piezoelectric element 31B is sandwiched between the second electrode ring portion 37A and the first electrode ring portion 35B. Additionally, the piezoelectric element 31C is held between the first electrode ring portion 35B and the second electrode ring portion 37B, and the piezoelectric element 31D is held between the second electrode ring portion 37B and the first electrode ring portion 35C. Thus, the respective piezoelectric elements 31A to 31D are held between the first electrode portion 32 and the second electrode portion 33.

Further, the ultrasonic transducer 22 includes insulation rings 38A and 38B. The insulation ring 38A is placed on the distal direction side of the first electrode ring portion 35A of the first electrode portion 32. The insulation ring 38B is placed on the proximal direction side of the first electrode ring portion 35C of the first electrode portion 32. The transducer mounting portion 27 is inserted through the respective insulation rings 38A and 38B. Furthermore, the ultrasonic transducer 22 includes a back mass 36. The back mass 36 is placed on the proximal direction side of the insulation ring 38B. The piezoelectric elements 31A to 31D, the first electrode portion 32, the second electrode portion 33, and the insulation rings 38A and 38B are pressed toward the distal direction by the back mass 36. Consequently, the piezoelectric elements 31A to 31D, the first electrode portion 32, the second electrode portion 33, and the insulation rings 38A and 38B are held between the horn member 23 and the back mass 36.

FIG. 5 is a view showing an electrical connection state between the ultrasonic transducer 22 which is a vibration generating section and the electric power source 26. As shown in FIG. 5, the electric power source 26 is electrically connected to the first electrode portion 32 by the electrical wiring portion 25A. Further, the electric power source 26 is electrically connected to the second electrode portion 33 by the electrical wiring portion 25B. When the vibration generating electric power P is output from the electric power source 26, a vibration generating voltage V is applied between the first electrode portion 32 and the second electrode portion 33. When the vibration generating voltage V is applied, a vibration generating current I flows through the piezoelectric elements 31A to 31D sandwiched between the first electrode portion 32 and the second electrode portion 33. That is, on the basis of the vibration generating electric power P from the electric power source 26, the vibration generating current I is supplied to the ultrasonic vibrator 22 from the electric power source 26. The vibration generating current I is an alternating current whose current direction periodically changes. Furthermore, an ultrasonic impedance value Z which is an impedance value of the vibration generating electric power P is represented by Expression (1).

[Expression 1]

$$Z=V/I=V^2/P \qquad (1)$$

FIG. 6 and FIG. 7 are views showing configurations of the treatment section 17 and the jaw 18. Here, FIG. 6 shows a state where the jaw 18 is opened relative to the treating section 17, and FIG. 7 shows a state where a treated target is not present between the jaw 18 and the treatment section 17 and the jaw 18 is closed relative to the treatment section 17. Moreover, FIG. 7 shows a cross section perpendicular to the longitudinal axis C. As shown in FIG. 6 and FIG. 7, the jaw 18 includes a jaw main body 41 whose proximal portion is attached to the sheath 8, and a grasp member 42 attached to the jaw main body 41. The jaw main body 41 and the grip member 42 are formed of, e.g., a metal having electrical conductivity. Additionally, the jaw 18 includes a pad member 43 attached to the grasp member 42. The pad member 43 is made of, e.g., PTFE having electrical insulation properties.

A contact portion (a contact surface) 45, which is contactable with the treatment section 17 in a state where the jaw 18 is closed relative to the treatment section 17, is formed on the pad member 43. When the jaw 18 is closed relative to the treatment section 17 in a state where no treated target is present between the jaw 18 and the treatment section 17, the abutment portion 45 of the pad member 43 comes into contact with the treatment section 17. The contact portion 45 is opposed to the treatment section 17. Moreover, in this embodiment, the abutment section 45 is perpendicular to an opening direction (a direction of an arrow A1 in each of FIG. 6 and FIG. 7) and a closing direction (a direction of an arrow A2 in each of FIG. 6 and FIG. 7) of the jaw 18.

Here, two directions which are perpendicular (transverse) to the longitudinal axis C and also perpendicular to the opening and closing directions of the jaw 18 are defined as a first width direction (a direction of an arrow B1 in FIG. 7) and a second width direction (a direction of an arrow B2 in FIG. 7). An inclined facing portion 46A that faces the treatment section 17 in a state where it is inclined relative to the contact portion 45 is formed on the first width direction side of the contact portion 45 by the grasp member 42. Further, an inclined facing portion 46B opposed to the treatment section 17 in a state where it is inclined relative to the abutment portion 45 is formed on the second width direction side of the contact portion 45 by the grip member 42. In a state where the contact section 45 is in abutment with the treatment section 17, the inclined facing portions 46A and 46B are apart from the treatment section 17. Thus, in a state where the contact portion 45 is in contact with the treatment section 17, the grasp member 42 does not come into contact with the treatment section 17.

As shown in FIG. 3, the control unit 3 includes a control section 51 electrically connected to the electric power source 26. A switch section 47 is provided in the fixed handle 12. Opened and closed states of the switch section 47 are changed over on the basis of input of an energy operation using the energy operation input button 16. The switch section 47 is connected to the control section 51 through a signal path portion 48 extended through the transducer case 21 and an inside of the cable 7. When the switch section 47 is closed, an operation signal is transmitted to the control section 51 through the signal path portion 48. The control section 51 includes an ultrasonic control section 58. The ultrasonic control section 58 controls an output state of the vibration generating electric power P from the electric power source 26 on the basis of the transmitted operation signal.

Furthermore, the control unit 3 includes an impedance detecting section 52 electrically connected to the electric power source 26 and the control section 51, and a peak detecting section 53 electrically connected to the impedance detecting section 52 and the control section 51. In a state where the vibration generating electric power P is output from the electric power source 26, the impedance detecting section 52 detects an ultrasonic impedance value Z of the vibration generating electric power P with time.

The peak detecting section 53 detects a peak of the ultrasonic impedance value Z (a target peak) on the basis of changes with time of the detected ultrasonic impedance value Z. The peak detecting section 53 includes a gradual decrease detecting section 55, a tentative peak value holding section 56, and a peak judging section 57. Details of the gradual decrease detecting section 55, the tentative peak value holding section 56, and the peak judging section 57 will be described later. Moreover, the control unit 3 includes a notifying section 59 such as a buzzer or a lamp. The notifying section 59 is electrically connected to the control section 51. Details of the notifying section 59 will be described later. Additionally, an explanation of the target peak and a detection method of the target peak will be also described later. It is to be noted that the impedance detecting section 52 is, e.g., a detection circuit. Furthermore, each of the control section 51 and the peak detecting section 53 is formed of, e.g., a processor including a CPU (Central Processing Unit) or an ASIC (application specific integrated circuit) or a logic circuit such as an FPGA (Field Programmable Gate Array), and a memory (a storage section).

A function and an effect of the ultrasonic treatment apparatus 1 will now be described later. At the time of giving a treatment to a treated target such as a biological tissue by using the ultrasonic treatment system 1, the sheath 8, the ultrasonic probe 9, and the jaw 18 are inserted into a body or the like in which a treated target is present. Further, the treatment section 17 and the jaw 18 are moved until the treated target is placed between the jaw 18 opened relative to the treating section 17 and the treatment section 17. Furthermore, when the movable handle 13 is closed relative to the fixed handle 12, the treated target is grasped between the treatment section 17 and the jaw 18.

In this state, an energy operation is input by the energy operation input button 16, an operation signal is transmitted to the control section 51, and output of the vibration generating electric power P from the electric power source 26 begins. When the vibration generating electric power P is supplied, the vibration generating current I is converted into an ultrasonic vibration by the piezoelectric elements 31A to 31D. The ultrasonic vibration generated by the ultrasonic transducer 22 is transmitted to the treatment section 17 through the horn member 23 and the ultrasonic probe 9, and the treatment section 17 longitudinally vibrates. When the treatment section 17 longitudinally vibrates in a state where the treated target is griped between the treatment section 17 and the jaw 18, frictional heat is generated between the treated target and the treatment section 17. The frictional heat enables coagulating and simultaneously incising the treated target.

When a treatment is given to the treated target held between the treatment section 17 and the jaw 18, cut-and-divided of the treated target occurs in at least a part range of the treated target in the transmitting direction of the ultrasonic vibration. FIG. 8 is a view for explaining the cut-and-divided of the treated target H grasped between the treatment section 17 and the jaw 18. It is to be noted the cut-and-divided occurs over the entire range of the treated target in the transmitting direction (the longitudinal axial direction) of the ultrasonic vibration in some cases, or it occurs only in a part range the treated target in the transmitting direction (the longitudinal axis direction) of the ultrasonic vibration in some cases. In a region where the cutoff has occurred, the treated target H is divided at a dividing face D that is parallel to the transmitting direction of the ultrasonic vibration and also parallel to the opening and closing directions of the jaw (a direction of an arrow A1 in FIG. 8 and a direction of an arrow A2 in FIG. 8). The dividing face D is perpendicular to the first width direction (a direction of an arrow B1 in FIG. 8) and a second width direction (a direction of an arrow B2 in FIG. 8). Thus, in the range where the cut-and-divided has occurred, the treated target H is divided into a region H1 on the first width direction side of the dividing face D and a region H2 on the second width direction side of the dividing face D.

In the range where the treated target H is divided by the cut and divided, the contact section 45 of the jaw 18 comes into contact with the treatment section 17. When the treatment section 17 vibrates (longitudinally vibrates) by the ultrasonic vibration in a state where the abutment section 45 of the jaw 18 is in contact with the treatment section 17, the contact section 45 of the jaw 18 is worn. Thus, it is important to appropriately judge whether the treated target H has been cut and divided. It is to be noted that, when the treated target is divided only in a part of the range of the treated target H in the transmitting direction (the longitudinal axis direction) of the ultrasonic vibration, the treated target H is not divided in a remaining part of the range of the treated target H in the transmitting direction of the ultrasonic vibration.

Figure 9:
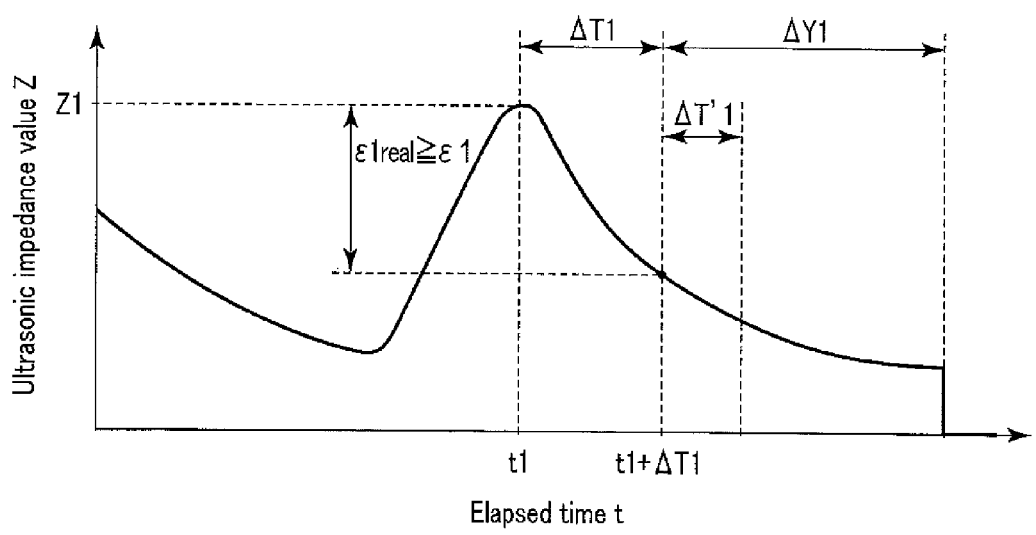
FIG. 9 is a schematic view showing an example of changes with time of an ultrasonic impedance value from a start of output of a vibration generating electric power from the electric power source according to the first embodiment.

Here, the ultrasonic impedance value Z of the vibration generating electric power P changes in accordance with a load to the ultrasonic probe 9, i.e., a load to the ultrasonic transducer 22 connected to the ultrasonic probe 9. FIG. 9 shows an example of changes with time in an ultrasonic impedance value Z from an output start of the vibration generating electric power P from the electric power source 26. In FIG. 9, an axis of ordinate represents the ultrasonic impedance value Z, and an axis of abscissa represents an elapsed time t from an output start of the vibration generating electric power P. Pressing force to the treatment section 17 from the jaw 18 gradually increases up to the vicinity of a time point at which the treated target H is cut-and-divided due to, e.g., changes in a state of the treated target H between the contact portion 45 of the jaw 18 and the treatment section 17. As a result, the load to the ultrasonic probe 9 is gradually increases. Thus, the ultrasonic impedance value Z gradually increases with time until the treatment target H is cut-and-divided. Here, the term of the gradual increase with time means that the ultrasonic impedance value Z gradually increases as the elapsed time t advances, and it also includes that the ultrasonic impedance value Z gradually increases while including a small increase or decrease of tens of $\Omega$ or less.

When the treated target H is cut-and-divided, since the contact portion 45 of the jaw 18 is placed near the treatment section 17, a surface of the pad member 43 (the contact portion 45) denatures due to frictional heat generated by the ultrasonic vibration of the treatment section 17. Thus, the load to the ultrasonic probe 9 is gradually decreased. Therefore, the ultrasonic impedance value Z gradually decreases subsequent to the vicinity of the time point where the treated target H is cut off. Here, gradually decreasing with time means that the ultrasonic impedance value Z gradually decreases as the elapsed time t advances, and it also includes that the ultrasonic impedance value Z gradually decreases while including a small increase or decrease of tens of $\Omega$ or less.

Since the ultrasonic impedance value Z changes due to the cut-and-divided as described above, the ultrasonic impedance value Z becomes a peak (a maximal value) with time in the vicinity of a time point when the treated target H is cut-and-divided (for example, in the vicinity of a time point when the contact portion 45 of the jaw 18 begins to come into contact with the treatment section 17). When the time-dependent peak of the ultrasonic impedance value Z is detected, it can be appropriately judged whether the treated target H has been cut-and-divided. Here, in the example shown in FIG. 9, an ultrasonic impedance value Z1 becomes a target peak which is a peak (peak value) caused due to the cut-and-divided of the treated target H. Further, an elapsed time t1 is a target peak point at which the target peak is produced.

Figure 10:
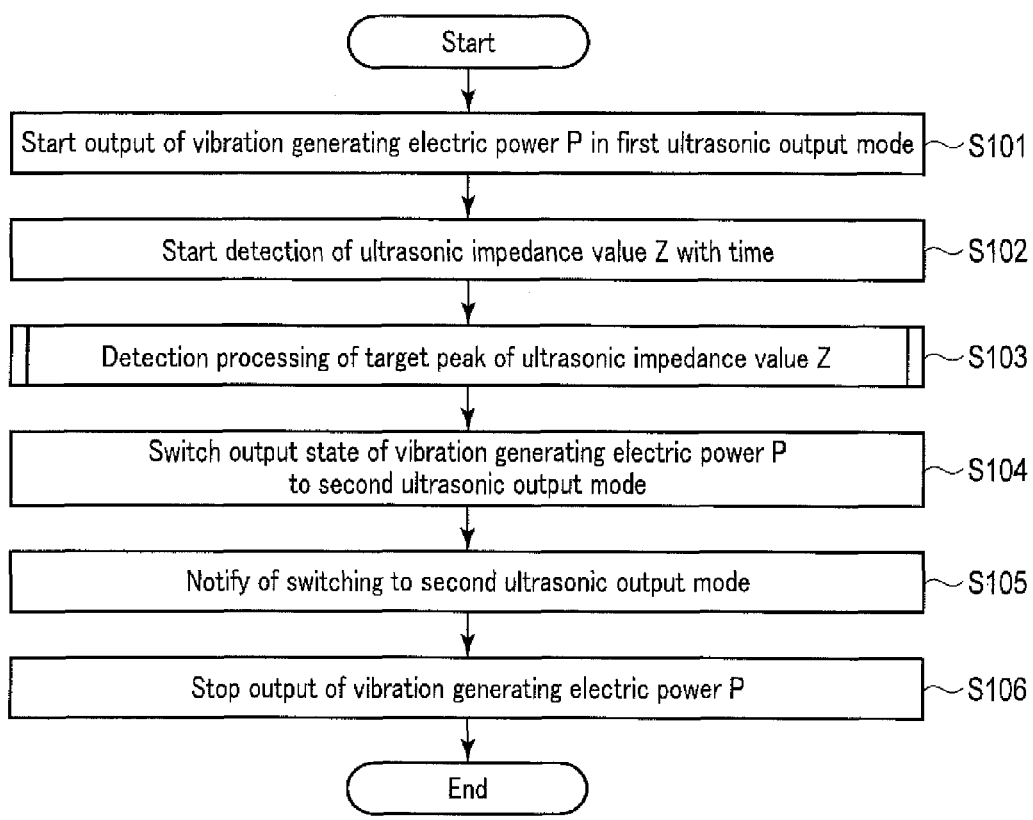
FIG. 10 is a flowchart showing an actuating state of the control unit from a start of output of the vibration generating electric power according to the first embodiment in a detection allowed state.
Figure 11:
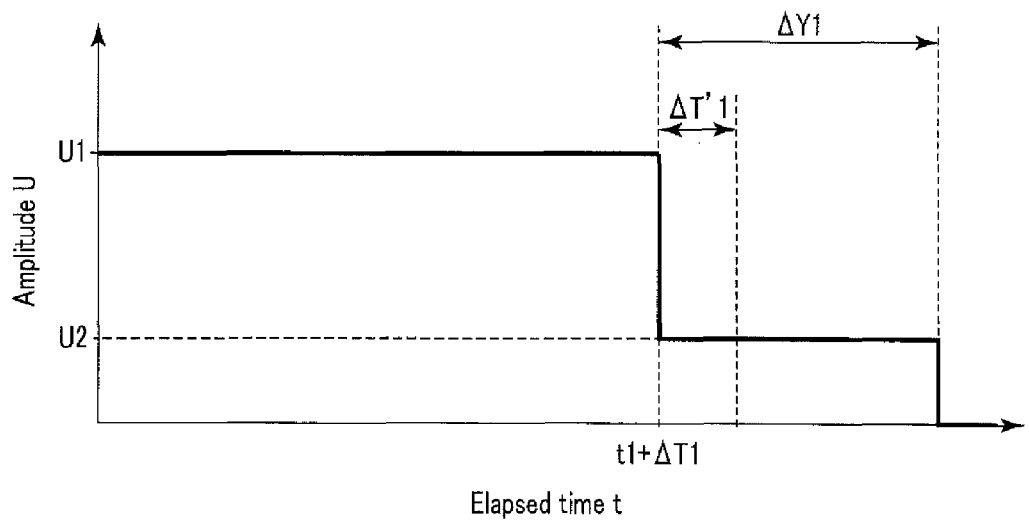
FIG. 11 is a schematic view showing an example of changes with time of an amplitude of an ultrasonic vibration in the treatment section according to the first embodiment.

FIG. 10 is a view (a flow) showing an actuating state of the control unit 3 from a start of output of the vibration generating electric power P. Further, FIG. 11 shows changes with time of an amplitude U of the ultrasonic vibration in the treatment section 17 (e.g., the distal end of the ultrasonic probe 9) in an example where the ultrasonic impedance value Z changes with time as shown in FIG. 9. In FIG. 11, an axis of ordinate represents the amplitude U of the ultrasonic vibration, and an axis of abscissa represents an elapsed time t from the start of output of the vibration generating electric power P. As shown in FIG. 10, in a first ultrasonic output mode, output of the vibration generating electric power P from the electric power source 26 is started (a step S101). In this embodiment, in the first ultrasonic output mode, the ultrasonic control section 58 controls an output state of the vibration generating electric power P by constant-current control to maintain a current value of the vibration generating current I (an effective value of an alternating current) at a fixed first current value I1. Thus, the vibration generating electric power P (the vibration generating voltage V) is adjusted to a state where the vibration generating current has the fixed first current value I1 in correspondence with a change in the ultrasonic impedance value Z.

Here, the amplitude U of the ultrasonic vibration in the treatment section 17 is proportionate to the current value of the vibration generating current I. In the first ultrasonic output mode, since the vibration generating current I is maintained at the first current value I1, the treatment section 17 vibrates with a fixed first amplitude U1 as shown in FIG. 11. It is to be noted that, in regions other than the treatment section 17 (e.g., the proximal end of the ultrasonic probe 9, or the horn member 23), the amplitude of the ultrasonic vibration is likewise proportionate to the current value of the vibration generating current I.

When output of the vibration generating electric power P is started in the first ultrasonic output mode, the impedance detecting section 52 starts detection of the ultrasonic impedance value Z of the vibration generating electric power P with time (a step S102). Consequently, the ultrasonic impedance value Z is detected with time. In this embodiment, in the first ultrasonic output mode, to adjust the amplitude of the ultrasonic vibration in the treatment section 17 to the fixed first amplitude U1, the constant-current control by which the vibration generating current I has the fixed first current value I1 is performed. Thus, changes with time of at least one of the vibration generating electric power P and the vibration generating voltage V are detected, and the ultrasonic impedance value Z is calculated by using Expression (1) on the basis of the detected vibration generating electric power P and/or the vibration generating voltage V. Consequently, the ultrasonic impedance value Z is detected with time. Moreover, in a given example, the impedance detecting section 52 detects the vibration generating voltage V and the vibration generating current I with time, and calculates the ultrasonic impedance value Z by using Expression (1).

Additionally, the peak detecting section 53 executes detection processing of a target peak of the ultrasonic impedance value Z produced due to the cut-and-divided of the treated target H based on the changes with time of the ultrasonic impedance value Z (a step S103). At this time, a target peak point at which the ultrasonic impedance value Z becomes the target peak (a target peak value) may be detected.

Figure 12:
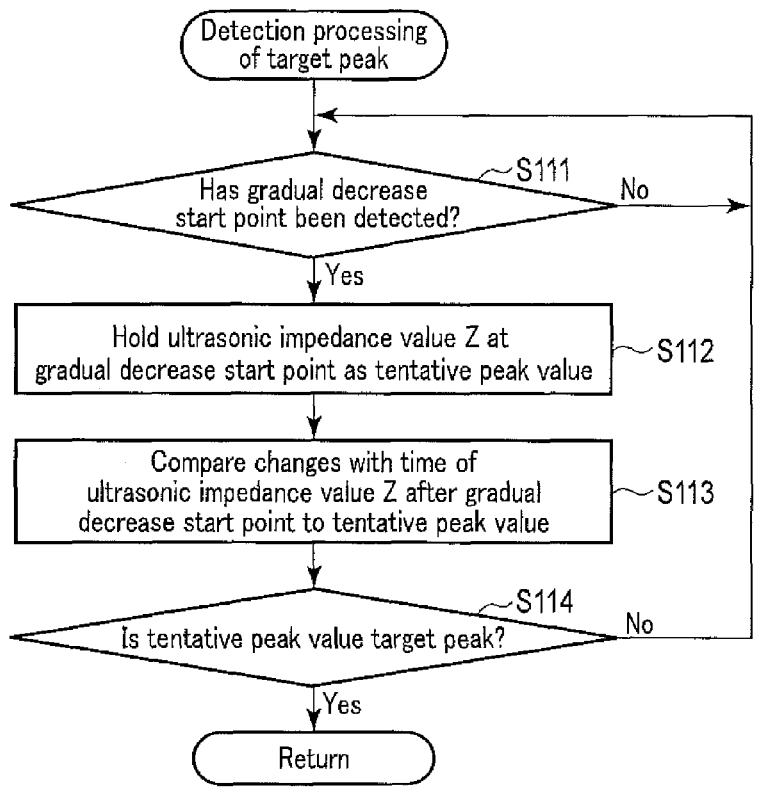
FIG. 12 is a flowchart showing detection processing of a target peak executed by a peak detecting section according to the first embodiment.

FIG. 12 is a view showing the detection processing (the step S103 in FIG. 10) of the target peak of the ultrasonic impedance value Z executed by the peak detecting section 53. That is, FIG. 12 shows a method of detecting the target peak by the peak detecting unit 53 in the detection allowing state. As shown in FIG. 12, in the detection processing of the target peak, first, the gradual decrease detecting section 55 detects a gradual decrease start point at which the ultrasonic impedance value Z starts to gradually decrease based on a detection result of the ultrasonic impedance value Z in the impedance detecting unit 52 (a step S111). In the example shown in FIG. 9, the elapsed time t1 is detected as the gradual decrease start point. When the gradual decrease start point is detected (the step S111—Yes), the tentative peak value holding section 56 holds the ultrasonic impedance value Z at the detected gradual decrease start point as a tentative peak value (a step S112). In the example shown in FIG. 9, the ultrasonic impedance value Z1 at the elapsed time t1 is held as the tentative peak value.

Furthermore, the peak judging section 57 compares changes with time of the ultrasonic impedance value Z after the gradual decrease start point with respect to the held tentative peak value (a step S113). In the example shown in FIG. 9, changes with time of the ultrasonic impedance value Z after the elapsed time t1 are compared to the ultrasonic impedance value Z1 held as the tentative peak value. Moreover, on the basis of the comparison of the changes with time of the ultrasonic impedance value Z relative to the tentative peak value, the peak judging section 57 judges whether the tentative peak value is the target peak caused due to the cut and divided of the treated target H (a step S114). In the example shown in FIG. 9, a judgment is made upon whether the ultrasonic impedance value Z1 held as the tentative peak value is the target peak (the target peak value). At this time, whether the detected gradual decrease start point is a target peak point may be judged. In the example shown in FIG. 9, the elapsed time t1 which is the gradual decrease start point is determined to be the target peak point at a time point which is the elapsed time t1+ΔT1.

In a given example, at a step S113 (comparison processing) in FIG. 12, whether a decrement $\epsilon$real of the ultrasonic impedance value Z from the tentative peak value is equal to or higher than the reference decrement $\epsilon$ after elapse of the reference time Δt from the decrease start point is determined by comparison. Furthermore, at the step S113, whether the ultrasonic impedance value Z has continuously become smaller than the tentative peak value after the gradual decrease start point is determined by comparison. In this example, when the decrement $\epsilon$real of the ultrasonic impedance value Z from the tentative peak value is equal to or higher than the reference decrement $\epsilon$ after elapse of the reference time ΔT from the gradual decrease start point and the ultrasonic impedance value Z continuously falls below the tentative peak value, the tentative peak value is determined to be the target peak. In the example shown in FIG. 9, after the gradual decrease start point t1, the ultrasonic impedance value Z continuously falls below the tentative peak value Z1. Further, a decrement $\epsilon$1real of the ultrasonic impedance value Z during elapse of a reference time ΔT1 from the elapsed time t1 which is the gradual decrease start point is equal to or higher than a reference decrement $\epsilon$1. Thus, in the example shown in FIG. 9, the peak judging section 57 determines that the tentative peak value Z1 is the target peak. Therefore, it is determined that at least a part of the treatment target U has been cut off at a time point of the elapsed time t1 (a time point when the tentative peak value Z1 was detected).

Furthermore, in another example, at the step S113, whether the ultrasonic impedance value Z gradually increases after the gradual decrease start point may be judged. Moreover, when the ultrasonic impedance value Z gradually increases after the gradual decrease start point, whether an increment $\xi$real of the ultrasonic impedance value Z from a gradual increase start point at which gradual increase begins is equal to or higher than a reference increment $\xi$ is judged at the step S113. In this example, when the decrement $\epsilon$real of the ultrasonic impedance value Z from the tentative peak value is equal to or higher than the reference decrement $\epsilon$ after elapse of the reference time ΔT from the gradual decrease start point and the increment $\xi$real of the ultrasonic impedance value Z from the gradual increase start point does not become equal to or higher than the reference increment $\xi$, the tentative peak value is determined to be the target peak. In the example shown in FIG. 9, after the gradual decrease start point t1, the ultrasonic impedance value Z does not gradually increase. Additionally, the decrement $\epsilon$1real of the ultrasonic impedance value Z during elapse of the reference time ΔT is equal to or higher than the reference decrement $\epsilon$1 without increasing beyond the reference increment $\xi$ from the elapsed time t1 which is the gradual decrease start point. Thus, in the example shown in FIG. 9, the tentative peak value Z1 is determined to be the target peak.

It is to be noted that, in the foregoing example, a length of the reference time ΔT, magnitude of the reference decrement $\epsilon$, and magnitude of the reference increment $\xi$ are not determined as prescribed values, and they may be set in correspondence with, e.g., changes with time of the ultrasonic impedance value Z. Thus, values of the reference time ΔT, the reference decrement $\epsilon$, and the reference increment $\xi$ change depending on situations. Further, the comparison of changes with time of the ultrasonic impedance value Z after the gradual decrease start point with respect to the tentative peak value (the step S113) and the judgement on whether the tentative peak value is the target peak value (the step S114) are not restricted to the foregoing example.

As described above, when the comparison of changes with time of the ultrasonic impedance value Z after the gradual decrease start point with respect to the tentative peak value (the step S113) and the judgement on whether the tentative peak value is the target peak value (the step S114) are carried out, the target peak caused by the cut and divided of the treated target H is detected. The target peak is detected after elapse of the reference time ΔT from the target peak point. Thus, a peak detection point at which the target peak is detected is a time point after the target peak point, and the target peak is not detected at the target peak point at which the ultrasonic impedance value Z reaches the target peak. In the example shown in FIG. 9, the elapsed time t1+ΔT1 is the peak detection point at which the target peak is detected.

Further, for example, when the treated target H is thick (a dimension of the treated target H is large in the opening and closing directions of the jaw 18), a peak of the ultrasonic impedance value Z is produced at a moment when the abutment section 45 of the jaw 18 comes into contact with the treated target H and a contact surface of the treated target H to the jaw 17 starts to be incised. In this embodiment, since the target peak is detected as described above, a peak produced due to the contact of the contact section 45 with the treated target H is determined not to be the target peak. Thus, even if a peak different from the target peak is produced before the target peak, the target peak is appropriately detected.

When the peak produced due to the cutoff of the treated target H is detected in compliance with the flow shown in FIG. 10 (the steps S101 to S103), the ultrasonic control section 58 switches an output state of the ultrasonic electric power P from the electric power source 26 from the first ultrasonic output mode to the second ultrasonic output mode (a step S104). Thus, in the second ultrasonic output mode, the vibration generating electric power P is output. In this embodiment, at the peak detection point when the target peak is detected, the first ultrasonic output mode is switched to the second ultrasonic output mode. Thus, at a time point when at least a prescribed time ΔT' elapses from the peak detection point, the vibration generating electric power P is output in the the second ultrasonic output mode. In an example shown in FIG. 11 (FIG. 9), the first ultrasonic output mode is switched to the second ultrasonic output mode at a peak detection point t1+ΔT1, and hence the vibration generating electric power P is output in the second ultrasonic output mode at the time point when a prescribed time ΔT'1 elapses from the peak detection point t1+ΔT1.

According to this embodiment, in the second ultrasonic output mode, the ultrasonic control section 58 controls the output state of the vibration generating electric power P on the basis of the constant-current control which maintains the current value of the vibration generating current I (an effective value of an alternating current) at a fixed second current value I2 smaller than the first current value I1. Thus, the vibration generating electric power P (the vibration generating voltage V) is adjusted in correspondence with a change in the ultrasonic impedance value Z so that the vibration generating current I has the fixed second current value I2. As described above, the amplitude U of the ultrasonic vibration in the treatment section 17 is proportionate to the current value of the vibration generating current I. In the second ultrasonic output mode, since the vibration generating current I is maintained at the second current value I2, as shown in FIG. 11, the treatment section 17 vibrates with a fixed second amplitude U2 smaller than a first amplitude U1. A ratio of the second amplitude U2 to the first amplitude U1 is, e.g., 20% to 80%. Since the amplitude of the treatment section 17 is adjusted as described above in the first ultrasonic output mode and the second ultrasonic output mode, when an average of the amplitudes U of the treatment section 17 provided by the ultrasonic vibration during a predetermined unit time is an average amplitude Uave, the average amplitude Uave of the treatment section 17 during the predetermined unit time in the second ultrasonic output mode is smaller than that in the first ultrasonic output mode.

It is to be noted that the ultrasonic control section 58 may directly adjust the current value of the vibration generating current I in the first ultrasonic output mode and the second ultrasonic output mode, and the current value of the vibration generating current I may be changed by adjusting an electric power value of the vibration generating electric power P. Thus, the ultrasonic control section 58 changes the amplitude U of the ultrasonic vibration in the treatment section 17 between the first ultrasonic output mode and the second ultrasonic output mode by adjusting at least one of the electric power value of the vibration generating electric power P and the current value of the vibration generating current I.

Here, assuming that a vibration velocity of the treatment section 17 provided by the ultrasonic vibration is v and a resonance frequency of the ultrasonic vibration is F, Expression (2) is achieved.

[Expression 2]

$$v \propto U \cdot F \qquad (2)$$

That is, the vibration velocity v is proportionate to a product of the amplitude U and the resonance frequency F. As described above, the second amplitude U2 of the treatment section 17 in the second ultrasonic output mode is smaller than the first amplitude U1 of the treatment section 17 in the first ultrasonic output mode. Thus, assuming that an average of the vibration velocities v of the treatment section 17 provided by the ultrasonic vibration during a predetermined unit time is an average vibration velocity vave, the average vibration velocity vave of the treatment section 17 during the predetermined unit time in the second ultrasonic output mode is smaller than that in the first ultrasonic output mode.

When the average vibration velocity vave of the treatment section 17 during the predetermined unit becomes small, a heat quantity of frictional heat generated by the vibration of the treatment section 17 in a treatment for the treated target H is reduced. When the heat quantity of the frictional heat is reduced, incision performance provided by the ultrasonic vibration in the treatment section 17 is decreased in the treatment for the treated target H. Thus, the incision performance provided by the ultrasonic vibration in the treatment section 17 in the second ultrasonic output mode is smaller than that in the first ultrasonic output mode before the peak detection point. However, in the second ultrasonic output mode, likewise, since the treatment section 17 vibrates, the treated target H is coagulated and incised at the same time by the frictional heat.

Here, even if the treated target H is divided (cut off) only in a part of a range of the treated target H in a transmitting direction (the longitudinal axis direction) of the ultrasonic vibration, the abutment section 45 of the jaw 18 comes into contact with the treatment section 17 in the range where the treated target H is divided. Thus, even if the treated target H is divided and cut off only in a part of the range of the treated target H in the longitudinal axis direction, a target peak arising from the cut and divided is produced. In this case, in a remaining part of the range of the treated target H in the transmitting direction of the ultrasonic vibration, the treated target H is not divided at the peak detection point. Thus, when the output of the vibration generating electric power P from the electric power source 26 is stopped at the peak detection point, a remaining part of the treated target H which is not divided in a dividing face D which is parallel to the transmitting direction (the longitudinal axis direction) of the ultrasonic vibration and also parallel to the opening and closing directions of the jaw 18 is produced in a remaining part of the range of the treated target H.

Thus, in this embodiment, even at and after the peak detection point, the vibration generating electric power P is output from the electric power source 26 in the second ultrasonic output mode. Thus, even after the peak detection point, the treatment section 17 vibrates (longitudinally vibrates), and frictional heat is generated in the treatment section 17. Therefore, even if the treated target H is not divided in a part of the range at the peak detection point, the treated target H is coagulated and incised at the same time in an undivided part of the range by the frictional heat. Consequently, the treated target H is divided in the dividing face D even in an undivided part of the range at the peak detection point. As described above, it is possible to effectively prevent an uncut part from being produced in the treated target H.

Furthermore, in the second ultrasonic output mode, since the treatment section 17 vibrates with the small second amplitude U2, as described above, the average vibration velocity vave of the treatment section 17 during the predetermined unit time is decreased, and the heat quantity of the frictional heat generated by the vibration of the treatment section 17 is reduced. Thus, even if the treatment section 17 vibrates in the second ultrasonic output mode at and after the peak detection point, worn and thermal deformation of the pad member 43 (the contact section 45) are reduced in a region where the abutment section 45 comes into contact with the treatment section 17.

As shown in FIG. 10, when the output state of the vibration generating electric power P from the electric power source 26 is switched to the second ultrasonic output mode (the step S104), the notifying section 59 notifies that the output state of the vibration generating electric power P from the electric power source 26 has been switched from the first ultrasonic output mode to the second ultrasonic output mode (a step S105). Here, sound is emitted when the notifying section 59 is a buzzer, or lighting is performed when the notifying section 59 is a lamp. An operator judges whether the treated target H is cut and divided with the use of the notifying section 59, and also recognizes that switching to the second ultrasonic output mode has been carried out. Moreover, the output of the vibration generating electric power P from the electric power source 26 is stopped (a step S106). The output of the vibration generating electric power P may be manually stopped by the surgeon, or it may be automatically stopped after elapse of a predetermined output time ΔY from the peak detection point (the start of the output of the vibration generating electric power P in the second ultrasonic output mode). In the example shown in FIG. 11, after elapse of a predetermined output time ΔY1 from a peak detection point t1+ΔT1, the output of the vibration generating electric power P is automatically stopped.

In the ultrasonic treatment apparatus 1 according to this embodiment, the gradual decrease start point of the ultrasonic impedance value Z is detected, and the ultrasonic impedance value Z at the gradual decrease start point is held as a tentative peak value. Additionally, whether the held tentative peak value is the target peak which is a detection target is judged by comparing changes with time of the ultrasonic impedance value Z after the gradual decrease start point with respect to the tentative peak value. Thus, the target peak can be appropriately detected irrespective of magnitude of the target peak (the target peak value) produced due to the cut and divided. Therefore, in the treatment for the treated target H grasped between the treatment section 17 and the jaw 18 using the ultrasonic vibration, whether the treated target H is cut and divided can be appropriately judged.

Further, in this embodiment, even at and after the peak detection point, the vibration generating electric power P is output from the electric power source 26 in the second ultrasonic output mode. Thus, even after the peak detection point, the treatment section 17 vibrates (longitudinally vibrates), and frictional heat is generated in the treatment section 17. Therefore, even if the treated target H is not divided in a part of the range at the peak detection point, the treated target H is coagulated and incised at the same time in an undivided part of the range by the frictional heat. Consequently, it is possible to effectively prevent an uncut part from being produced in the treated target H.

Furthermore, in the second ultrasonic output mode, since the treatment section 17 vibrates with the small second amplitude U2, the heat quantity of the frictional heat generated by the vibration of the treatment section 17 is reduced. Thus, even if the treatment section 17 vibrates in the second ultrasonic output mode after the peak detection point, worn and thermal deformation of the pad member 43 (the contact section 45) can be reduced in a region where the abutment section 45 comes into abutment with the treatment section 17.

Modification

Figure 13:
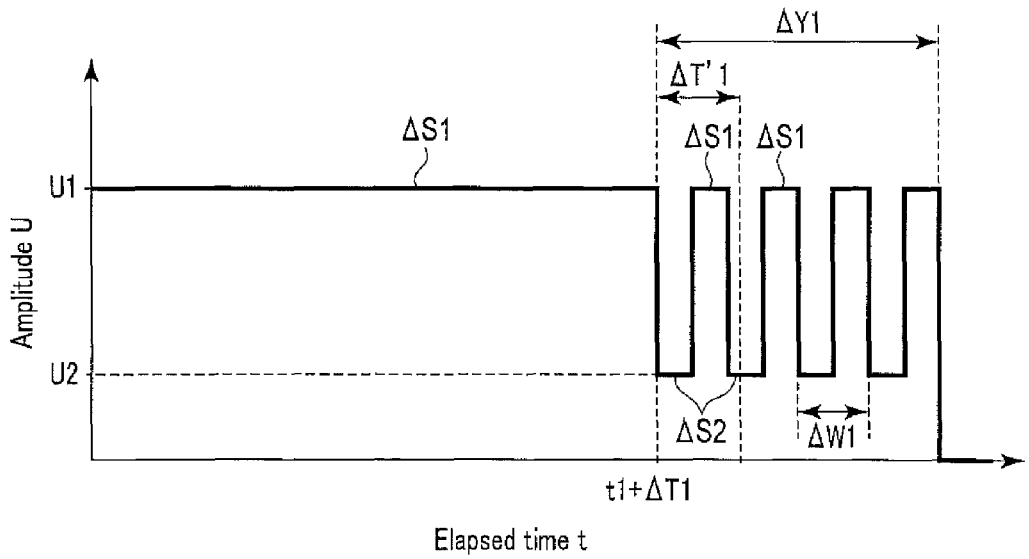
FIG. 13 is a schematic view showing an example of changes with time of an amplitude of the ultrasonic vibration in the treatment section according to a first modification.

It is to be noted that, in the first embodiment, although the amplitude of the treatment section 17 is maintained constant at the second amplitude U2 in the second ultrasonic output mode, it is not restricted thereto. For example, as a first modification, the amplitude U of the ultrasonic vibration in the treatment section 17 (e.g., the distal end of the ultrasonic probe 9) may change with time in the second ultrasonic output mode as shown in FIG. 13. FIG. 13 shows changes with time of the amplitude U of the ultrasonic vibration in the treatment section 17 (e.g., the distal end of the ultrasonic probe 9) in an example where the ultrasonic impedance value Z changes with time as shown in FIG. 9. In FIG. 13, an axis of ordinate represents the amplitude U of the ultrasonic vibration, and an axis of abscissa represents an elapsed time t from the start of output of the vibration generating electric power P.

Here, a vibration state where the treatment section 17 vibrates with the fixed first amplitude U1 is defined as a first vibration stage ΔS1, and a vibration state where the treatment section 17 vibrates with a fixed second amplitude U2 smaller than the first amplitude U1 is defined as a second vibration stage ΔS2. In this modification, the vibration state of the treatment section 17 is continuously maintained as the first vibration stage ΔS1 in the first ultrasonic output mode. Thus, in the first ultrasonic output mode, the treatment section 17 vibrates with the fixed first amplitude U1. The ultrasonic control section 58 changes the amplitude U of the ultrasonic vibration in the treatment section 17 between the first vibration stage ΔS1 and the second vibration stage ΔS2 by adjusting at least one of the electric power value of the vibration generating electric power P and the current value of the vibration generating current I.

Furthermore, in the second ultrasonic output mode, the vibration state provided by the ultrasonic vibration of the treatment section 17 periodically changes between the first vibration stage ΔS1 and the second vibration stage ΔS2. That is, in the second ultrasonic output mode, the vibration state of the treatment section 17 is modulated (changed) in a modulation cycle (a cycle) ΔW. It is to be noted that the modulation cycle (an ultrasonic modulation cycle) ΔW coincides with an elapsed time from the start of the first vibration stage ΔS1 to the start of the next first vibration stage ΔS1 (from the start of the second vibration stage ΔS2 to the start of the next second vibration stage ΔS2). In the example shown in FIG. 13, the vibration state of the treatment section 17 changes in the modulation cycle ΔW1 in the second ultrasonic output mode. Here, a proportion of the first vibration stage ΔS1 in the modulation cycle (one cycle) ΔW is a duty ratio γ of the first vibration stage ΔS1. In the second ultrasonic output mode, a ratio of the second amplitude U2 to the first amplitude U1 is, e.g., 20% to 80%, and the duty ratio γ of the first vibration stage ΔS1 is, e.g., 25% to 75%. It is to be noted that the first vibration stage ΔS1 is continuously held in the first ultrasonic output mode, the duty ratio γ of the first vibration stage ΔS1 is 100%.

As described above, the duty ratio γ of the first vibration stage ΔS1 changes between the first ultrasonic output mode and the second ultrasonic output mode. Thus, in the second ultrasonic output mode, a time ratio τ of the first vibration stage ΔS1 to the second vibration stage ΔS2 is smaller than that in the first ultrasonic output mode. Since the time ratio τ of the first vibration stage ΔS1 where the amplitude U of the treatment section 17 increases is reduced, the average amplitude Uave of the treatment section 17 during a predetermined unit time in the second ultrasonic output mode is smaller than that in the first ultrasonic output mode. Thus, on the basis of Expression (2) and others described in the first embodiment, in this modification, likewise, the average amplitude velocity vave of the treatment section 17 during the predetermined unit time in the second ultrasonic output mode is smaller than that in the first ultrasonic output mode.

Since the average vibration velocity vave of the treatment section 17 during the predetermined unit time is reduced, in this modification, likewise, a heat quantity of the frictional heat generated by the vibration of the treatment section 17 in the treatment for the treated target H is decreased in the second ultrasonic output mode. When the heat quantity of the frictional heat is reduced, the incision performance provided by the ultrasonic vibration in the treatment section 17 is lowered in the treatment for the treated target H. Thus, in the second ultrasonic output mode, the incision performance provided by the ultrasonic vibration in the treatment section 17 is smaller than that in the first ultrasonic output mode before the peak detection point. However, in this modification, like the first embodiment, since the treatment section 17 vibrates in the second ultrasonic output mode, the treated target H is coagulated and incised at the same time by the frictional heat.

Figure 14:
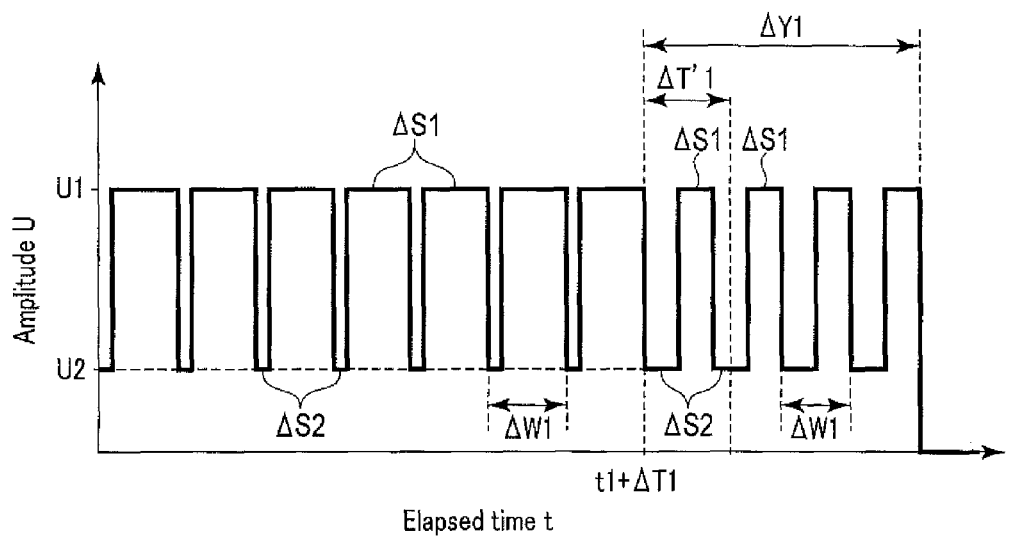
FIG. 14 is a schematic view showing an example of changes with time of an amplitude of the ultrasonic vibration in the treatment section according to a second modification.

For example, as a second modification, the amplitude U of the ultrasonic vibration in the treatment section 17 (e.g., the distal end of the ultrasonic probe 9) may change with time in the first ultrasonic output mode as shown in FIG. 14. FIG. 14 shows changes with time of the amplitude U of the ultrasonic vibration in the treatment section 17 (e.g., the distal end of the ultrasonic probe 9) in an example where the ultrasonic impedance value Z changes with time as shown in FIG. 9. In FIG. 14, an axis of ordinate represents the amplitude U of the ultrasonic vibration, and an axis of abscissa represents an elapsed time t from the start of output of the vibration generating electric power P.

In this modification, the vibration state provided by the ultrasonic vibration of the treatment section 17 likewise periodically changes between the first vibration stage ΔS1 and the second vibration stage ΔS2 in the first ultrasonic output mode in addition to the second ultrasonic output mode. In the first ultrasonic output mode, the vibration state of the treatment section 17 is modulated (changed) in the same modulation cycle (a cycle) ΔW as that in the second ultrasonic output mode. In the example shown in FIG. 14, in both the first ultrasonic output mode and the second ultrasonic output mode, the modulation cycle of the change in the vibration state of the treatment section 17 between the first vibration stage ΔS1 and the second vibration stage ΔS2 is ΔW1. In this modification, likewise, a proportion γ of the first vibration stage ΔS1 in the modulation cycle ΔW (that is, a duty ratio of the first vibration stage ΔS1) in the first ultrasonic output mode is higher than that in the second ultrasonic output mode. The duty ratio γ of the first vibration stage ΔS1 in the first ultrasonic output mode is, e.g., 80% to 90%, and the duty ratio γ of the first vibration stage ΔS1 in the second ultrasonic output mode is, e.g., 30% to 40%.

As described above, since the duty ratio γ of the first vibration stage ΔS1 changes between the first ultrasonic output mode and the second ultrasonic output mode, in this modification, a time ratio τ of the first vibration stage ΔS1 to the second vibration stage ΔS2 in the second ultrasonic output mode is smaller than that in the first ultrasonic output mode like the first modification. Thus, in the second ultrasonic output mode, the average amplitude Uave of the treatment section 17 during a predetermined unit time is smaller than that in the first ultrasonic output mode, and the average amplitude velocity vave of the treatment section 17 during the predetermined unit time is smaller than that in the first ultrasonic output mode. Thus, in the second ultrasonic output mode, the incision performance provided by the ultrasonic vibration in the treatment section 17 is smaller than that in the first ultrasonic output mode at and before the peak detection point. However, according to this modification, like the first embodiment, in the second ultrasonic output mode, since the treatment section 17 vibrates, the treated target H is coagulated and incised at the same time by the frictional heat.

Figure 15:
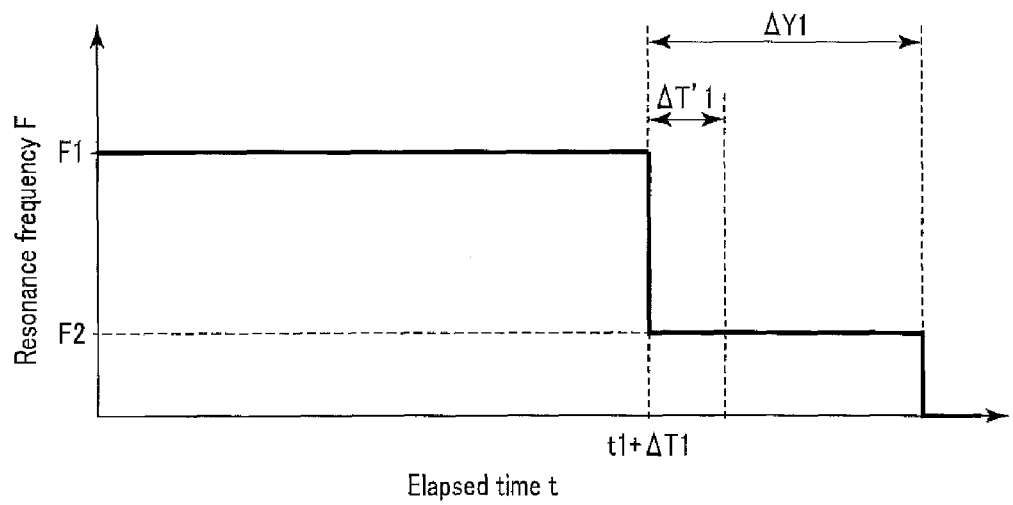
FIG. 15 is a schematic view showing an example of changes with time of a resonance frequency of the ultrasonic vibration in a vibration transmitting section according to a third modification.

Furthermore, as a third modification, the amplitude U of the treatment section 17 does not have to change between the first ultrasonic output mode and the second ultrasonic output mode as shown in FIG. 15. Instead, in this modification, a resonance frequency F of the ultrasonic vibration changes between the first ultrasonic output mode and the second ultrasonic output mode. FIG. 15 shows changes with time of the resonance frequency F of the ultrasonic vibration in an example where the ultrasonic impedance value Z changes with time as shown in FIG. 9. In FIG. 15, an axis of ordinate represents the resonance frequency F of the ultrasonic vibration, and an axis of abscissa represents an elapsed time t from the start of output of the vibration generating electric power P.

As shown in FIG. 15, in this modification, the ultrasonic probe 9 (the treatment section 17) vibrates at a first resonance frequency F1 in the first ultrasonic output mode, and the ultrasonic probe 9 (the treatment section 17) vibrates at a second resonance frequency F2 smaller than the first resonance frequency F1 in the second ultrasonic output mode. The resonance frequency F1 of the ultrasonic vibration is, e.g., 47 kHZ in the first ultrasonic output mode, and the second resonance frequency F2 of the ultrasonic vibration is 23.5 kHz, which is ½ of the first resonance frequency F1, in the second ultrasonic output mode. When the second resonance frequency F2 is set to ½ of the first resonance frequency F1, the vibration transmitting section (the horn member 23 and the ultrasonic probe 9) can be vibrated in a state where the proximal end of the vibration transmitting section (the proximal end of the horn member 23) and the distal end of the vibration transmitting section (the distal end of the ultrasonic probe 9) are antinode positions of the ultrasonic vibration in both the first ultrasonic output mode and the second ultrasonic output mode. It is to be noted that the resonance frequency of the ultrasonic vibration varies by changing a frequency of the vibration generating current I.

According to this modification, in the second ultrasonic output mode, the resonance frequency F of the ultrasonic vibration is smaller than that in the first ultrasonic output mode. On the basis of Expression (2) described in the first embodiment, the vibration velocity v of the treatment section 17 is proportionate to a product of the amplitude U and the resonance frequency F. When the resonance frequency F becomes small, in the second ultrasonic output mode, the average vibration velocity vave of the treatment section 17 in a predetermined unit time becomes smaller than that in the first ultrasonic output mode. Thus, in the second ultrasonic output mode, the incision performance provided by the ultrasonic vibration in the treatment section 17 is smaller than that in the first ultrasonic output mode before the peak detection point. However, according to this modification, like the first embodiment, in the second ultrasonic output mode, since the treatment section 17 vibrates, the treated target H is coagulated and incised at the same time by the frictional heat.

Further, in the foregoing embodiment and the modifications, although switching to the second ultrasonic output mode having the low incision performance is performed at the peak detection point, it is not restricted thereto. For example, as a fourth modification, switching to the second ultrasonic output mode having the low incision performance may be performed when a set time ΔY' passes from the peak detection point as shown in FIG. 16 and FIG. 17. FIG. 16 is a view (a flow) showing an actuating state of the control unit 3 after the start of output of the vibration generating electric power P in this modification. Furthermore, FIG. 17 shows changes with time of the amplitude U of the ultrasonic vibration in the treatment section 17 (e.g., the distal end of the ultrasonic probe 9) in an example where the ultrasonic impedance value Z changes with time as shown in FIG. 9. In FIG. 17, an axis of ordinate represents the amplitude U of the ultrasonic vibration, and an axis of abscissa represents an elapsed time t from the start of output of the vibration generating electric power P.

As shown in FIG. 16 and FIG. 17, in this modification, when the target peak is detected by the detection processing of the target peak of the ultrasonic impedance value Z (the step S103), an output state of the vibration generating electric power P from the electric power source 26 is switched to a third ultrasonic output mode (a step S121). That is, at the peak detection point, the output of the vibration generating electric power P in the third ultrasonic output mode is started. Moreover, the vibration generating electric power P is output in the third ultrasonic output mode only during a set time ΔY' from the peak detection point. Additionally, when the set time ΔY' passes from a switching point of the output state of the vibration generating electric power P to the third ultrasonic output mode (a step S122—Yes), the output state of the vibration generating electric power P is switched to the second ultrasonic output mode having small incision performance (the average vibration velocity vave in the treatment section 17). That is, at a time point when the set time ΔY' passes from the start of the output in the third ultrasonic output mode (the peak detection point), the output of the vibration generating electric power P in the second output mode is started.

Here, the set time ΔY' is smaller than the prescribed time ΔT', and it is a micro time. That is, the time during which the vibration generating electric power P is output in the third ultrasonic output mode is short. Thus, in this modification, like the first embodiment, at a time point when at least the prescribed time ΔT' passes from the peak detection point, the vibration generating electric power P is output in the second ultrasonic output mode. In an example shown in FIG. 17, the vibration generating electric power P is output in the third ultrasonic output mode only during the set time ΔY'1 shorter than the prescribed time ΔT'1 from the peak detection point t1+ΔT1. Further, at a time point when the set time ΔY'1 passes from the peak detection point t1+ΔT1, switching to the second ultrasonic output mode is performed. It is to be noted that the set time ΔY' is, e.g., 1 to 2 seconds.

According to this modification, the treatment section 17 vibrates with the fixed first amplitude U1 in the first ultrasonic output mode, and the treatment section 17 vibrates with the fixed second amplitude U2 smaller than the first amplitude U1 in the second ultrasonic output mode. Furthermore, in the third ultrasonic output mode, the treatment section 17 vibrates with a third amplitude U3 larger than the first amplitude U1. Since the amplitude U of the treatment section 17 changes as described above, in the third ultrasonic output mode, the average amplitude Uave of the treatment section 17 during the predetermined unit time is larger than those in the first ultrasonic output mode and the second ultrasonic output mode. Thus, on the basis of Expression (2) described in the first embodiment, in the third ultrasonic output mode, the average vibration velocity vave of the treatment section 17 during the predetermined unit time is higher than that in the first ultrasonic output mode. Thus, in the third ultrasonic output mode, the incision performance provided by the ultrasonic vibration in the treatment section 17 is higher than that in the first ultrasonic output mode before the peak detection point.

In this modification, the vibration generating electric power P is output from the electric power source 26 in the third ultrasonic output mode having the high incision performance (having the high average vibration velocity vave) only during the small set time ΔY' from the peak detection point. Thus, even if the treated target H is not divided in a part of the range at the peak detection point, the treated target H is instantaneously coagulated and incised at the same time and after the peak detection point in an undivided part of the range. Consequently, it is possible to effectively prevent an uncut part from being produced in the treated target H.

Moreover, the set time ΔY' during which the vibration generating electric power P is output in the third ultrasonic output mode is small, and the vibration generating electric power P is output in the second ultrasonic output mode having the low incision performance at a time point when at least the prescribed time ΔT' passes from the peak detection point. Thus, in this modification where the output is performed in the third ultrasonic output mode, likewise, worn and thermal deformation of the pad member 43 (the contact section 45) can be reduced in a region where the abutment section 45 comes into abutment with the treatment section 17.

Additionally, in a given modification, after the start of output of the ultrasonic electric power P, a frequency f of the ultrasonic vibration may be adjusted by PLL (Phase Locked Loop) control. In this case, after the start of adjustment at which the adjustment of the frequency f of the ultrasonic vibration starts, detection processing of a minimal value of the ultrasonic impedance value Z is carried out. Here, assuming that a time point at which a minimal value Z is first detected after the start of adjustment of the frequency f is a minimal detection point, a detection disallowed state where the detection of a target peak is not executed is switched to a detection allowed state where the detection of the target peak is executed by the control section 51 at the minimal detection point. That is, the peak detecting section 53 is controlled so that the detection of the target peak is not executed until the minimal detection point.

Furthermore, in another modification in which the frequency f is adjusted by the PLL control, at the time of startup which is a time point reached after elapse of a predetermined set time from the adjustment start point of the frequency f, the control section 51 may switch the detection disallowed state where the detection of the target peak is not performed to the detection allowed state where the detection of the target peak is executed. That is, in this modification, the peak detecting section 53 is controlled so that the detection of the target peak is not executed until the startup point.

Moreover, in a given modification, a switching operating section which inputs a switching operation between the detection disallowed state (a non-detection state) where the peak detecting section 53 does not execute the detection and judgement (determination) of the target peak and the detection allowed state where the peak detecting section 53 executes the detection of the target peak may be provided in the control unit 3 or the like.

Additionally, in addition to the ultrasonic vibration, a high-frequency electric power may be used in a treatment for the treated target H. In this case, the high-frequency electric power is transmitted to the treatment section 17 and the jaw 18, and the treatment section 17 and the jaw 18 function as electrodes. Further, when a high-frequency current flows through the treated target H griped between the treatment section 17 and the jaw 18, the treated target (a biotissue) H is denatured, and coagulation of the treated target H is promoted.

In the foregoing embodiment and modifications, the ultrasonic treatment apparatus (1) includes the impedance detecting section (52) configured to detect the ultrasonic impedance value (Z) of the vibration generating electric power (P) with time in a state where the vibration generating electric power (P) is output from the electric power source (26), and the gradual decrease detecting section (55) configured to detect the gradual decrease start point at which the ultrasonic impedance value (Z) starts to gradually decrease on the basis of a detection result in the impedance detecting section (52). Furthermore, the ultrasonic treatment apparatus (1) includes the tentative peak value holding section (56) configured to hold the ultrasonic impedance value (Z) at the detected gradual decrease start point as a tentative peak value, and the peak judging section (57) configured to judge whether the held tentative peak value is a target peak which is a detection target by comparing changes with time of the ultrasonic impedance value (Z) after the gradual decrease start point with respect to the held tentative peak value. Moreover, the ultrasonic treatment apparatus (1) includes the ultrasonic control section (58) configured to control the electric power source (26) to output the vibration generating electric power (P) in the second ultrasonic output mode where the incision performance provided by the ultrasonic vibration in the treatment section (17) is smaller than that in the first ultrasonic output mode before the peak detection point when at least the prescribed time (ΔT') elapses from the peak detection point at which the target peak is detected on the basis of a determination in the peak judging section (57).

Hereinafter, a characteristic matter will be added.

Remark

Additional Matter 1

A control unit of an ultrasonic treatment apparatus, the ultrasonic treatment apparatus including a vibration generating section configured to generate ultrasonic vibration when a vibration generating electric power is supplied, a treatment section to which the ultrasonic vibration generated in the vibration generating section is transmitted and which is configured to perform a treatment by use of the transmitted ultrasonic vibration, and a jaw that is openable and closable relative to the treatment section and that includes a contact section contactable with the treatment section in a state where the jaw is closed relative to the treatment section, a control unit being configured to control a supply of the vibration generating electric power to the vibration generating section, the control unit comprising:

an electric power source which is configured to output the vibration generating electric power, an impedance detecting section which is configured to detect an ultrasonic impedance value of the vibration generating electric power with time, in a state where the vibration generating electric power is output from the electric power source, a gradual decrease detecting section which is configured to detect a gradual decrease start point at which the ultrasonic impedance value starts to gradually decrease on the basis of detection results in the impedance detecting section, a tentative peak value holding section which is configured to hold the ultrasonic impedance value at the detected gradual decrease start point as a tentative peak value, a peak judging section which is configured to judge whether or not the held tentative peak value is a target peak of a detection target by comparing, to the held tentative peak value, changes with time of the ultrasonic impedance values after the gradual decrease start point, and an ultrasonic control section which is configured to controls an output state of the vibration generating electric power from the electric power source, the ultrasonic control section being configured to output the vibration generating electric power from the electric power source in a second ultrasonic output mode where incision performance provided by the ultrasonic vibration in the treatment section becomes smaller than that in a first ultrasonic output mode before a peak detection point on the basis of a determination in the peak judging section, when at least a prescribed time passes from the peak detection point at which the target peak is detected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
an electric power source configured to output a vibration generating electric power;
an ultrasonic transducer configured to generate an ultrasonic vibration when the vibration generating electric power is supplied from the electric power source;
a treatment section which is configured to perform a treatment by use of the ultrasonic vibration generated in the ultrasonic transducer;
a jaw which is openable and closable relative to the treatment section, and which includes a contact section contactable with the treatment section in a state where the jaw is closed relative to the treatment section;
an impedance detecting section configured to detect an ultrasonic impedance value of the ultrasonic transducer with time, in a state where the vibration generating electric power is output from the electric power source;
a gradual decrease detecting section configured to detect a gradual decrease start point at which the ultrasonic impedance value starts to gradually decrease on the basis of detection results in the impedance detecting section;

a tentative peak value holding section configured to hold the ultrasonic impedance value at the detected gradual decrease start point as a tentative peak value;

a peak judging section configured to judge whether or not the held tentative peak value is a target peak of a detection target by comparing, to the held tentative peak value, changes with time of the ultrasonic impedance value after the gradual decrease start point; and an ultrasonic control section configured to control an output state of the vibration generating electric power from the electric power source, the ultrasonic control section being configured to output the vibration generating electric power from the electric power source in a second ultrasonic output mode where incision performance provided by the ultrasonic vibration in the treatment section becomes smaller than that in a first ultrasonic output mode before a peak detection point on the basis of a determination in the peak judging section, when at least a prescribed time passes from the peak detection point at which the target peak is detected.

2. The ultrasonic treatment apparatus according to claim 1,
wherein, in the second ultrasonic output mode, the ultrasonic control section is configured to control the output state of the vibration generating electric power from the electric power source so that an average vibration velocity of the treatment section provided by the ultrasonic vibration during a predetermined unit time becomes smaller than that in the first ultrasonic output mode.

3. The ultrasonic treatment apparatus according to claim 1,
wherein the ultrasonic control section is configured to control the output state of the vibration generating electric power from the electric power source so that the treatment section is vibrated with a fixed first amplitude in the first ultrasonic output mode and so that the treatment section is vibrated with a fixed second amplitude smaller than the first amplitude in the second ultrasonic output mode.

4. The ultrasonic treatment apparatus according to claim 1,
wherein the ultrasonic control section is configured to change an amplitude of the ultrasonic vibration in the treatment section between the first ultrasonic output mode and the second ultrasonic output mode by adjusting at least one of an electric power value of the vibration generation electric power and a current value of a vibration generating current supplied to the ultrasonic transducer from the electric power source on the basis of an output of the vibration generating electric power.

5. The ultrasonic treatment apparatus according to claim 1,
wherein, when a first vibration stage where the treatment section vibrates with a fixed first amplitude and a second vibration stage where the treatment section vibrates with a fixed second amplitude smaller than the first amplitude are defined, the ultrasonic control section is configured to control an output state of the vibration generating electric power from the electric power source so that a time ratio of the first vibration stage to the second vibration stage in the second ultrasonic output mode becomes smaller than that in the first ultrasonic output mode.

6. The ultrasonic treatment apparatus according to claim 5,
wherein the ultrasonic control section is configured to periodically change a vibration state provided by the ultrasonic vibration of the treatment section between the first vibration stage and the second vibration stage in the second ultrasonic output mode and, in the first ultrasonic output mode,
the ultrasonic control section is configured to periodically change the vibration state provided by the ultrasonic vibration of the treatment section between the first vibration stage and the second vibration stage with the same modulation cycle as that in the second ultrasonic output mode, and configured to increase a proportion of the first vibration stage in the modulation cycle to be higher than that in the second ultrasonic output mode, or configured to continuously maintain the vibration state provided by the ultrasonic vibration of the treatment section at the first vibration stage.

7. The ultrasonic treatment apparatus according to claim 1,
wherein, in the second ultrasonic output mode, the ultrasonic control section is configured to control the output state of the vibration generating electric power from the electric power source so that a resonance frequency of the ultrasonic vibration becomes smaller than that in the first ultrasonic output mode.

8. The ultrasonic treatment apparatus according to claim 1,
wherein the ultrasonic control section is configured to output the vibration generating electric power from the electric power source in a third ultrasonic output mode in which incision performance provided by the ultrasonic vibration in the treatment section increases to be higher than that in the first ultrasonic output mode only during a set time, which is shorter than the prescribed time, from the peak detection point, and configured to switch to the second ultrasonic output mode after an output in the third ultrasonic output mode.

9. The ultrasonic treatment apparatus according to claim 8,
wherein, in the third ultrasonic output mode, the ultrasonic control section is configured to control the output state of the vibration generating electric power from the electric power source so that an average vibration velocity of the treatment section provided by the ultrasonic vibration during a predetermined unit time becomes higher than that in the first ultrasonic output mode.

10. The ultrasonic treatment apparatus according to claim 1,
wherein the impedance detecting section is configured to detect a vibration generating current and a vibration generating voltage in the ultrasonic transducer with time, and configured to detect the ultrasonic impedance value on the basis of the detected vibration generating current and vibration generating voltage.

11. The ultrasonic treatment apparatus according to claim 1, further comprising a notifying section configured to notify that an output state of the vibration generating electric power from the electric power source has been switched after switching from the first ultrasonic output mode to the second ultrasonic output mode.

12. A control unit which is electrically connected with an ultrasonic treatment instrument, the ultrasonic instrument including a treatment section configured to treat a treated target by use of an ultrasonic vibration generated in an ultrasonic transducer, the control unit comprising:
- an electric power source configured to output a vibration generating electric power to activate the ultrasonic transducer;
- an impedance detecting section configured to detect an ultrasonic impedance value of the ultrasonic transducer with time on the basis of the vibration generating electric power output from the electric power source;
- a gradual decrease detecting section configured to detect a gradual decrease start point at which the ultrasonic impedance value starts to gradually decrease on the basis of detection results in the impedance detecting section;
- a tentative peak value holding section configured to hold the ultrasonic impedance value at the detected gradual decrease start point as a tentative peak value;
- a peak judging section configured to judge whether or not the held tentative peak value is a target peak of a detection target by comparing, to the held tentative peak value, changes with time of the ultrasonic impedance value after the gradual decrease start point; and
- an ultrasonic control section configured to control an output state of the vibration generating electric power from the electric power source, the ultrasonic control section being configured to output the vibration generating electric power from the electric power source in a second ultrasonic output mode where incision performance provided by the ultrasonic vibration in the treatment section becomes smaller than that in a first ultrasonic output mode before a peak detection point on the basis of a determination in the peak judging section, when at least a prescribed time passes from the peak detection point at which the target peak is detected.

* * * * *